(12) United States Patent
Witherington et al.

(10) Patent No.: US 7,410,984 B2
(45) Date of Patent: Aug. 12, 2008

(54) COMPOUNDS

(75) Inventors: Jason Witherington, Harlow (GB); Richard Leonard Elliott, Harlow (GB)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 415 days.

(21) Appl. No.: 10/524,028

(22) PCT Filed: Aug. 8, 2003

(86) PCT No.: PCT/JP03/10119

§ 371 (c)(1), (2), (4) Date: Feb. 9, 2005

(87) PCT Pub. No.: WO2004/014859

PCT Pub. Date: Feb. 19, 2004

(65) Prior Publication Data

US 2005/0288337 A1    Dec. 29, 2005

(30) Foreign Application Priority Data

Aug. 10, 2002    (GB) ................................. 0218630.2

(51) Int. Cl.
*C07D 211/72* (2006.01)
*A61K 31/44* (2006.01)

(52) U.S. Cl. ...................... 514/345; 546/190
(58) Field of Classification Search ................. 546/290, 546/291; 514/345
See application file for complete search history.

(56) References Cited

FOREIGN PATENT DOCUMENTS

WO    WO-00/37444 A1    6/2000

OTHER PUBLICATIONS

Chang L L et al. "The Discovery of Small Molecule Carbamates as Potent Dual Alpha4Beta1/Alpha4Beta7 Integrin Anatagonists" Bioorganic & Medicinal Chemistry Letters, Oxford, GB, vol. 12, No. 2, 2002, pp. 159-163.
Lobb et al., Expert Opinion on Investigational Drugs, vol. 8, pp. 935-945, (1999).
Sircar et al., Bioorganic & Medical Chemistry, vol. 10, pp. 2051-2066, (2002).
Butcher, E. C., Cell, vol. 67, pp. 1033-1036, (1991).
Harlan, J. M., Blood, vol. 65, No. 3, pp. 513-525, (1985).
Hemler, M. E., Annu. Rev. Immunol., vol. 8, pp. 365-400, (1990).
Osborn, L., Cell, vol. 62, pp. 3-6, (1990).
Springer, T. A., Nature, vol. 346, pp. 425-434, (1990).
Springer, T. A., Cell, vol. 76, pp. 301-314, (1994).
Wayner, E. A., J. of Cell Biology, vol. 105, pp. 1873-1884, (1987).
Bornstein, P., Ann. Rev. Biochem., vol. 49, pp. 957-1003, (1980).
Miller, E. J., Chemistry of the collagens and their distribution, in "Extracellular Matrix Biochemistry", K.A. Piez and H.A. Reddi, editors, Elsevier, Amsterdam, pp. 41-78, (1983).
Hynes, R. O., Cell, vol. 48, pp. 549-554, (1987).
Shimizu et al., Immun. Reviews, No. 114, pp. 109-143, (1990).
Hemler, M. E., J. of Bio. Chem., vol. 262, No. 24, pp. 11478-11485, (1987).
Bochner, B. S., J. Exp. Med., vol. 173, pp. 1553-1556, (1991).
Ibbotson et al., Nature Medicine, vol. 7, No. 4, pp. 465-470, (2001).
Elices et al., Cell, vol. 60, pp. 577-584, (1990).
Wayner et al., J. of Cell Biol., vol. 109, pp. 1321-1330, (1989).
Bayless et al., J. of Cell Science, vol. 111, pp. 1165-1174, (1998).
Cheng et al., Biochem. Pharmacology, vol. 22, pp. 3099-3108, (1973).

*Primary Examiner*—Zinna N Davis
(74) *Attorney, Agent, or Firm*—Birch, Stewart, Kolasch & Birch, LLP

(57) ABSTRACT

The present invention relates to novel pyridone derivatives capable of inhibiting $\alpha_4$ integrin mediated cell adhesion, processes for their preparation, compositions comprising them and their use in the treatment of diseases capable of being modulated by the inhibition of cell adhesion.

13 Claims, No Drawings

COMPOUNDS

TECHNICAL FIELD

The present invention relates to novel compounds, processes for their preparation, compositions comprising them and their use in the treatment of diseases capable of being modulated by the inhibition of cell adhesion. More particularly, the present invention relates to novel pyridone derivatives that inhibit $\alpha_4$ integrin mediated cell adhesion and which are useful for the treatment of chronic inflammatory diseases.

BACKGROUND ART

The multiple adhesive interactions between leukocytes and endothelial cells or extracellular matrix proteins are a key factor in the regulation of immunity and inflammation. The earliest events in the migration of leukocytes out of the vasculature at site of inflammation include leukocyte rolling followed by changes in integrin avidity, which lead to subsequent firm adhesion (for reviews see Butcher, *Cell* 67:1033-1036 (1991); Harlan, *Blood* 3:513-525 (1985); Hemler, *Annu. Rev. Immunol.* 8:365-400 (1990); Osborn, *Cell* 62:3-6 (1990); Shimizu et al., *Immunol. Rev.* 114:109-143 (1990); Springer, *Nature* 346:425-434 (1990); and Springer, *Cell* 76:301-314 (1994)). In response to chemotactic factors, the leukocytes migrate through two adjacent endothelial cells and into tissues that are composed, in part, of the extracellular matrix protein fibronectin (FN) (see Wayner et al., *J. Cell Biol.* 105:1873-1884 (1987)) and collagen (CN) (see Bornstein et al., *Ann. Rev. Biochem.* 49:957-1003 (1980); and Miller, Chemistry of the collagens and their distribution, in "Extracellular Matrix Biochemistry", K. A. Piez and A. H. Reddi, editors, Elsevier, Amsterdam, 41-78 (1983)). Important recognition molecules that participate in these adhesive reactions belong to the integrin gene superfamily (for reviews see Hemler, *Annu. Rev. Immunol.* 8:365-400 (1990); Hynes, *Cell* 48:549-554 (1987); Shimizu et al., *Immunol. Rev.* 114:109-143 (1990); and Springer, *Nature* 346:425-434 (1990)).

Integrins are heterodimers composed of non-covalently associated subunits, referred to as the alpha ($\alpha$) and beta ($\beta$) subunits. To date, 8 integrin $\beta$ subunits have been identified which can associate with 16 distinct $\alpha$ subunits to form 23 distinct integrins.

The $\alpha_4\beta_1$ integrin, also known as VLA-4 (Very Late Antigen-4), is constitutively expressed on the surface of leukocytes including lymphocytes, monocytes, eosinophils and basophils (see Hemler et al., *J. Bio. Chem.* 262:11478-11485 (1987); and Bochner et al., *J. Exp. Med.* 173:1553-1556 (1991)). VLA-4 is reported to be present on neutrophils from septic patients (see Ibbotson et al., *Nature Med.* 7:465-470 (2001)). VLA-4 binds to vascular cell adhesion molecule-1 (VCAM-1) on activated endothelial cells, resulting in extravasation of leukocytes (Elices et al., *Cell* 60:577-584 (1990)). Once the cells have reached the extravascular space, VLA-4 can bind to the connecting segment 1 (CS-1), an alternatively spliced region of the FN A chain (Wayne et al., *J. Cell Biol.* 109:1321-1330 (1989)). In addition, VLA-4 is known to bind to osteopontin, a protein upregulated in arteriosclerotic plaques (see Bayless et al., *J. Cell Science* 111: 1165-1174 (1998)).

DISCLOSURE OF INVENTION

A novel series of compounds has now been found which also inhibit $\alpha_4$ integrin mediated cell adhesion. The present invention therefore provides, in a first aspect, a compound of formula (I) or a pharmaceutically acceptable derivative thereof:

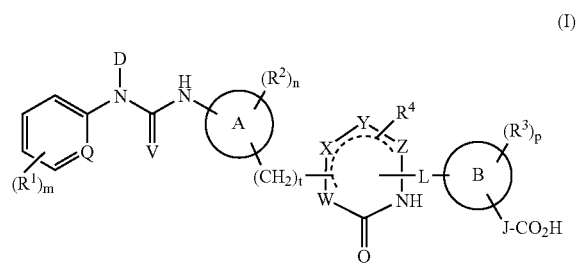

wherein

A and B are independently aryl or heteroaryl;

Q is C, CH or together with the group V or group D forms a 5-7 membered heterocyclic ring;

D is hydrogen, $C_{1-6}$alkyl or together with the group Q forms a 5-7 membered heterocyclic ring;

$R^1$, $R^2$ and $R^3$ are independently $C_{1-6}$alkyl, halogen, $C_{1-6}$alkoxy, hydroxy, cyano, $CF_3$, nitro, $C_{1-6}$alkylthio, amino, mono- or di-$C_{1-6}$alkylamino, carboxy, $C_{1-6}$alkanoyl, amido, mono- or di-$C_{1-6}$alkylamido, NHCOR$^9$ or NHSO$_2$R$^9$ in which R$^9$ is $C_{1-6}$alkyl, $C_{3-7}$cycloalkyl or phenyl (optionally substituted by up to three groups selected from $C_{1-6}$alkyl, halogen, $C_{1-6}$alkoxy, cyano, phenyl or $CF_3$) or is a group -E-(CH$_2$)$_{1-6}$NR$^x$R$^y$ in which E is a single bond or —OCH$_2$— and R$^x$ and R$^y$ are independently hydrogen, $C_{1-6}$alkyl or combine together to form a 5-7 membered heterocyclic ring;

$R^4$ is hydrogen, $C_{1-6}$alkyl, halogen or $C_{1-6}$alkoxy;

V is O, S, NH, N—$C_{1-6}$alkyl, NNO$_2$, NCN or together with the group Q forms a 5-7 membered heterocyclic ring;

W, X, Y and Z are independently C, CH or CH$_2$;

------ represents a single or double bond;

L is —(CH$_2$)$_q$— or —(CH$_2$)$_q$O— where q is 0, 1, 2 or 3 and q' is 2 or 3;

J is (i) a group —CR$^5$═CR$^6$— where R$^5$ and R$^6$ are independently hydrogen or $C_{1-6}$alkyl; or (ii) a group —CHR$^7$—CHR$^8$— where R$^7$ and R$^8$ are independently hydrogen, $C_{1-6}$alkyl, $C_{3-7}$cycloalkyl, aryl, heteroaryl, a group —NHCOR$^9$— or —NHSO$_2$R$^9$— in which R$^9$ is as defined above or a group —(CH$_2$)$_{1-6}$NR$^x$R$^y$— in which R$^x$ and R$^y$ are as defined above; or (iii) a single bond; or (iv) —CHR$^6$— where R$^6$ is as defined above; or (v) a group —O—CHR$^{10}$—, —NR$^{11}$—CHR$^{10}$— or —CR$^{12}$R$^{13}$—CHR$^{10}$— where R$^{10}$ and R$^{11}$ are independently hydrogen or $C_{1-6}$alkyl and R$^{12}$ and R$^{13}$ are independently $C_{1-6}$alkyl or R$^{12}$ and R$^{13}$ combine together to form a $C_{3-7}$cycloalkyl or a 5-7 membered heterocyclic ring;

m, n and p are independently 0, 1, 2 or 3; and t is 0, 1 or 2.

A particularly preferred sub-class of the compounds of formula (I) are the compounds of formula (Ia) or a pharmaceutically acceptable derivative thereof:

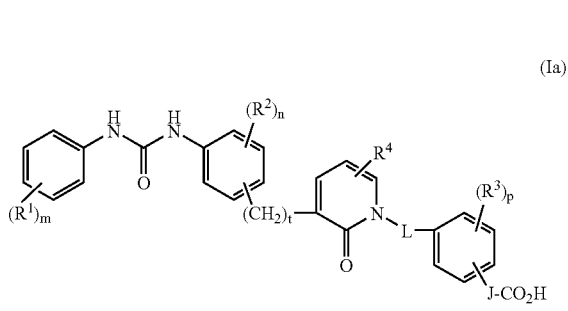

wherein:

$R^1, R^2, R^3, R^4$, L, J, m, n, p and t are as defined in formula (I).

Throughout the present specification, unless otherwise stated:

- the term "halogen" is used to describe a group selected from fluorine, chlorine, bromine or iodine;
- the term "$C_{1-6}$alkyl" is used to describe a group or a part of the group comprising a linear or branched alkyl group containing from 1 to 6 carbon atoms; examples of such groups include methyl, ethyl, propyl, isopropyl, n-butyl, isobutyl, tert butyl, pentyl or hexyl;
- the term "aryl" is used to denote phenyl and naphthyl (naphth-1-yl and naphth-2-yl) groups;
- the term "heteroaryl" is intended to mean an aromatic or a benzofused aromatic ring containing from 1 to 3 heteroatoms selected from oxygen, nitrogen and sulphur. Suitable examples of such aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such benzofused aromatic rings include quinolinyl, isoquinolinyl, indolyl, benzofuryl, benzothienyl, benzimidazolyl, benzoxazolyl and the like;
- the term "5-7 membered heterocyclic ring" is intended to mean a non-aromatic heterocyclic ring comprising 1-3 heteroatoms selected from nitrogen, oxygen and sulphur. Suitable examples of such rings include piperidinyl, piperazinyl, pyrrolidinyl and morpholinyl and the like. The heterocyclic rings are optionally substituted by $C_{1-6}$alkyl;
- the term "$C_{1-6}$ alkoxy" is used to describe a group or a part of the group wherein an oxygen atom is bound to the above-mentioned alkyl group; examples of such groups include methoxy, ethoxy, propoxy, isopropoxy, butoxy, isobutoxy, sec-butoxy and tert-butoxy, pentoxy or hexoxy;
- the term "$C_{1-6}$ alkanoyl" is used to describe groups formed by removing a "OH" group from the carboxyl group of a $C_{1-6}$ carboxylic acid; examples of such groups include formyl, acetyl, propionyl or butyryl; and
- the term "$C_{3-7}$ cycloalkyl" means a cyclic $C_{3-7}$ alkyl group; examples of such groups include cyclohexyl or cyclopentyl.

Within the Definition of the Compounds of Formula (I):

It will be appreciated that Q can be C not only when forming a 5-7 membered heterocyclic ring but also when substituted by an $R^1$ group;

When A and/or B is aryl a preferred group is phenyl. When A and/or B is heteroaryl a preferred group is pyridyl;

Suitably, A is phenyl or pyridyl;

Suitably, B is phenyl;

Suitably, $R^1$, $R^2$ and $R^3$ are independently $C_{1-6}$alkyl, halogen, $C_{1-6}$alkoxy, hydroxy, cyano, $CF_3$, nitro, $C_{1-6}$alkylthio, amino, mono- or di-$C_{1-6}$alkylamino, carboxy, $C_{1-6}$alkanoyl, amido, mono- or di-$C_{1-6}$alkylamido, $NHCOR^9$ or $NHSO_2R^9$ in which $R^9$ is $C_{1-6}$alkyl, $C_{3-7}$cycloalkyl or phenyl (optionally substituted by up to three groups selected from $C_{1-6}$alkyl, halogen, $C_{1-6}$alkoxy, cyano, phenyl or $CF_3$) or is a group -E-$(CH_2)_{1-6}NR^xR^y$ in which E is a single bond or —$OCH_2$— and $R^x$ and $R^y$ are independently hydrogen, $C_{1-6}$alkyl or combine together to form a ring including piperidinyl, piperazinyl, pyrrolidinyl or morpholinyl group in which a ring is optionally substituted by $C_{1-6}$alkyl;

When Q and V combine together to form a ring including piperidinyl, piperazinyl, pyrrolidinyl or morpholinyl group, which is optionally substituted by $C_{1-6}$alkyl;

When Q and D combine together to form a ring including piperidinyl, piperazinyl, pyrrolidinyl or morpholinyl group, which is optionally substituted by $C_{1-6}$alkyl; Suitably, J is:

(i) a group —$CR^5$=$CR^6$— where $R^5$ and $R^6$ are independently hydrogen or $C_{1-6}$alkyl; or (ii) a group —$CHR^7$—$CHR^8$— where $R^7$ and $R^8$ are independently hydrogen, $C_{1-6}$alkyl, $C_{3-7}$cycloalkyl, phenyl, naphthyl, thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl, pyridyl, quinolinyl, isoquinolinyl, indolyl, benzofuryl, benzothienyl, benzimidazolyl, benzoxazolyl, a group —$NHCOR^9$— or —$NHSO_2R^9$— in which $R^9$ is as defined above or a group —$(CH_2)_{1-6}NR^xR^y$— in which $R^x$ and $R^y$ are as defined above; or (iii) a single bond; or (iv) —$CHR^6$— where $R^6$ is as defined above; or (v) a group —O—$CHR^{10}$—, —$NR^{11}$—$CHR^{10}$— or —$CR^{12}R^{13}CHR^{10}$— where $R^{10}$ and $R^{11}$ are independently hydrogen or $C_{1-6}$alkyl and $R^{12}$ and $R^{13}$ are independently $C_{1-6}$alkyl or $R^{12}$ and $R^{13}$ combine together to form $C_{3-7}$ cycloalkyl, tetrahydropyranyl, piperidinyl, piperazinyl, pyrrolidinyl or morpholinyl;

When m, n or p is other than 0, preferred $R^1$, $R^2$ and $R^3$ groups respectively include $C_{1-6}$alkyl, halogen, $C_{1-6}$alkoxy, cyano or $CF_3$. When m, n or p is 2 or 3, the groups $R^1$, $R^2$ and $R^3$ respectively can be the same or different;

Preferably the ring containing W, X, Y and Z is

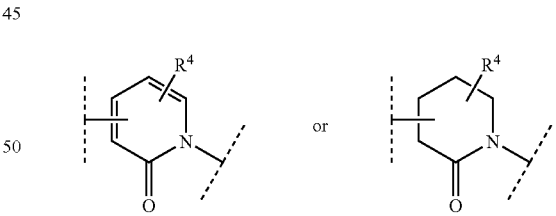

in which the ring nitrogen is bonded to the group L;

Preferably, $R^1$, $R^2$ and $R^3$ are independently $C_{1-6}$alkyl, halogen or $C_{1-6}$alkoxy;

When Q and V combine together to form a 5-7 membered heterocyclic ring, suitable examples are those in which Q and V form part of a benzimidazole or benzoxazole ring.

When Q and D combine together to form a 5-7 membered heterocyclic ring, suitable examples are those in which Q and D form part of an indoline ring;

Suitably, $R^4$ is hydrogen or halogen;

Preferably, Q is CH or C (when substituted by an $R^1$ group), V is O and D is hydrogen.

Suitably, L is —(CH$_2$)$_q$— where q is 0, 1, 2 or 3. Preferably L is —CH$_2$—. Preferably, J is
(i) a group —CR$^5$=CR$^6$— where R$^5$ and R$^6$ are independently hydrogen or C$_{1-6}$alkyl; or
(ii) a group —CHR$^7$—CHR$^8$— where R$^7$ and R$^8$ are independently hydrogen, C$_{1-6}$alkyl, C$_{3-7}$cycloalkyl, phenyl, a group —NHCOR$^9$— in which R$^9$ is C$_{1-6}$alkyl; or
(iii) a single bond;
(iv) —CHR$^6$— where R$^6$ is as defined above; or
(v) a group —O—CHR$^{10}$—, —NR$^{11}$—CHR$^{10}$— or —CR$^{12}$R$^{13}$CHR$^{10}$— where R$^{10}$ and R$^{11}$ are independently hydrogen or C$_{1-6}$alkyl and R$^{12}$ and R$^{13}$ are independently C$_{1-6}$alkyl or R$^{12}$ and R$^{13}$ combine together to form C$_{3-7}$ cycloalkyl group.

Preferably J is a group —CH=CH—, —(CH$_2$)$_2$—, —CHR$^7$—CH$_2$— where R$^7$ is C$_{1-6}$alkyl.

Within the Definition of Formula (Ia):

Suitably, R$^1$, R$^2$ and R$^3$ are independently C$_{1-6}$alkyl, halogen, C$_{1-6}$alkoxy, hydroxy, cyano, CF$_3$, nitro, C$_{1-6}$alkylthio, amino, mono- or di-C$_{1-6}$alkylamino, carboxy, C$_{1-6}$alkanoyl, amido, mono- or di-C$_{1-6}$alkylamido, NHCOR$^9$ or NHSO$_2$R$^9$ in which R$^9$ is C$_{1-6}$alkyl, C$_{3-7}$cycloalkyl or phenyl optionally substituted by up to three groups selected from C$_{1-6}$alkyl, halogen, C$_{1-6}$alkoxy, cyano, phenyl or CF$_3$;

When m is other than 0, preferred R$^1$ groups include halogen (particularly fluoro or chloro) or a C$_{1-6}$alkyl group (particularly methyl). When m is 2 or 3, the groups R$^1$ can be the same or different. Most preferably m is 1 and R$^1$ is a methyl group with an ortho relationship with respect to the urea moiety.

When n is other than 0, preferred R$^2$ groups include halogen (particularly fluoro or chloro), C$_{1-6}$alkyl group (particularly methyl) or a C$_{1-6}$alkoxy group (particularly methoxy). When n is 2 or 3, the groups R$^1$ can be the same or different. Most preferably n is 0 or n is 1 with R$^2$ being a methoxy group with an ortho relationship with respect to the urea moiety.

When p is other than 0, preferred R$^3$ groups include halogen (particularly fluoro or chloro) or a C$_{1-6}$alkyl group (particularly methyl). When p is 2 or 3, the groups R$^3$ can be the same or different.

R$^4$ is preferably hydrogen.

Suitably, L is —(CH$_2$)$_q$— where q is 0, 1, 2 or 3;
Suitably, J is
(i) a group —CR$^5$=CR$^6$— where R$^5$ and R$^6$ are independently hydrogen or C$_{1-6}$alkyl; or
(ii) a group —CHR$^7$—CHR$^8$— where R$^7$ and R$^8$ are independently hydrogen, C$_{1-6}$alkyl or a group —NHCOR$^9$— or —NHSO$_2$R$^9$— in which R$^9$ is as defined above;

Preferably, J is a group —CH=CH—, —(CH$_2$)$_2$—, —CHR$^7$—CH$_2$— in which R$^7$ is C$_{1-6}$alkyl;

Particularly preferred compounds of this invention include Examples E1-E51 (as described below) or a pharmaceutically acceptable derivative thereof. Especially preferred compounds of this invention include Examples E5, E9, E32, E41, E42 and E51 or a pharmaceutically acceptable derivative thereof.

It will be appreciated that the compounds of formula (I) have one or more asymmetric carbon atoms and therefore may occur as racemates, racemic mixtures and as individual enantiomers or diastereomers. All such isomeric forms are included within the present invention, including mixtures thereof.

Where a compound of the invention contains an alkenyl or alkenylene group, cis (Z) and trans (E) isomerism may also occur. The present invention includes the individual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallisation, chromatography or HPLC. A single stereoisomeric form of the agent may also be prepared from a corresponding optically pure intermediate or by resolution, such as HPLC of the corresponding racemate using a suitable chiral support or by fractional crystallisation of the diastereoisomeric salts formed by reaction of the corresponding racemate with a suitable optically active acid or base, as appropriate. Alternatively a mixture of enantiomers may be separated by chemical reaction with an appropriate chiral compound with the formation of a new covalently bonded species, for example the coupling of a racemic carboxylic acid with a chiral amine or alcohol to give a diastereomeric mixture (in the case of amides or esters respectively), which may be separated by conventional techniques such as column chromatography, HPLC or fractional crystallisation. The single diastereomers may then be converted to the single enantiomers of the desired compound by appropriate chemistry such as hydrolytic cleavage of the new covalent bond.

As used herein, the term "pharmaceutically acceptable derivative", means any pharmaceutically acceptable salt, solvate, or prodrug e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula (I). Further, in the case of a carboxylic acid (—COOH), esters may be employed, such as methyl esters, ethyl esters, double esters and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

The compounds of the present invention may be in the form of and/or may be administered as a pharmaceutically acceptable salt. For a review on suitable salts see Berge et al, J. Pharm. Sci., 1977, 66, 1-19.

Typically, a pharmaceutically acceptable salt may be readily prepared by using a desired acid or base as appropriate. The salt may precipitate from solution and be collected by filtration or may be recovered by evaporation of the solvent.

Suitable addition salts are formed from acids which form non-toxic salts and examples are hydrochloride, hydrobromide, hydroiodide, sulfate, bisulfate, nitrate, phosphate, hydrogen phosphate, acetate, maleate, malate, fumarate, lactate, tartrate, citrate, formate, gluconate, succinate, piruvate, oxalate, oxaloacetate, trifluoroacetate, saccharate, benzoate, methanesulfonate, ethanesulfonate, benzenesulfonate and p-toluensulfonate.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

In a further aspect, the present invention also provides a process for the preparation of a compound of formula (I) which comprises hydrolysis of a carboxylic acid ester derivative of formula (II):

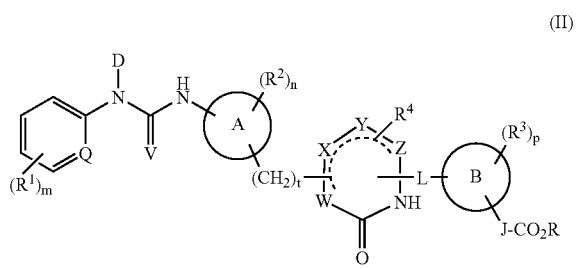

(II)

in which $R^1$-$R^4$, m, n, p, t, A, B, D, L, J, Q, V, W, X, Y and Z are as defined in formula (I) and R is a group capable of forming a carboxylic acid ester and optionally thereafter forming a pharmaceutically acceptable derivative thereof.

An example of a suitable R group is $C_{1-6}$alkyl such as methyl or t-butyl. Hydrolysis may either occur via an acidic or an alkaline medium. Such methods are familiar to those skilled in the art.

BEST MODE FOR CARRYING OUT THE INVENTION

The compounds of formula (II) can be prepared by either:
(a) reacting the compounds of formula (III)

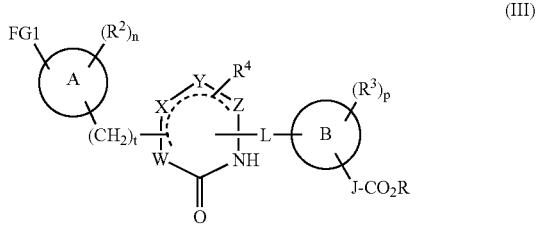

(III)

in which $R^2$-$R^4$, n, p, t, A, B, L, J, R, W, X, Y and Z are as defined in formula (I) or (II) with a compound of formula (IV)

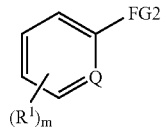

(IV)

in which $R^1$, m and Q are as defined above and FG1 and FG2 contain appropriate functional groups which are capable of reacting together to form the urea moiety; or
(b) reacting the compound of formula (III) in which FG1 is $NH_2$ as defined above with the compound of formula (V)

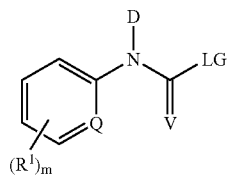

(V)

in which $R^1$, D and m are as defined for formula (I), Q and V combine to form a 5-7 membered heterocyclic ring and LG is a leaving group.

(c) reacting the compound of formula (VI)

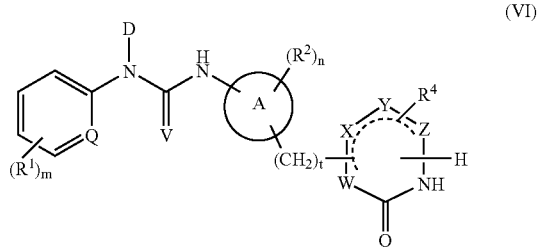

(VI)

in which $R^1$, $R^2$, $R^4$, m, n, t, A, B, D, Q, R, V, W, X, Y and Z are as defined in formula (I) or (II) with a compound of formula (VI)

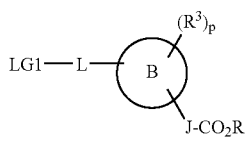

(VII)

in which p, R, $R^3$, J, B, and L are as defined in formula (I) or (II) in which J is as defined above and LG1 is a leaving group.

For process (a), suitable examples of appropriate FG1 and FG2 groups include:
(i) FG1 is —N═C═O and FG2 is $NH_2$; or FG1 is $NH_2$ and FG2 is N═C═O; or
(ii) FG1 is $NH_2$ and FG2 is $NH_2$ together with an appropriate urea forming agent.

In process (i) the reaction is typically carried out in an inert solvent such as dichloromethane or acetonitrile at ambient temperature.

In process (ii) the reaction is typically carried out in the presence of an appropriate urea forming agent, such as carbonyl diimidazole or phosgene, a suitable solvent being an inert organic solvent such as dimethylformamide, tetrahydrofuran, or dichloromethane at ambient or elevated temperature optionally in the presence of a base such as triethylamine or pyridine.

For process (b), a suitable example of a leaving group is halogen, particularly chloro. Examples of such reactions include those described by Jung et al. (J. Med. Chem., 1991, 34(3), 1110 and Passerini (J. Chem. Soc., 1954, 2256).

For process (c), a suitable example of a leaving group is halogen, particularly chloro. The reaction is typically carried out in an inert solvent such as tetrahydrofuran or acetonitrile at ambient temperature.

Intermediate compounds of formulae (III), (IV), (V), (VI) and (VII) are either commercially available or can be prepared using methods described herein, by methods known to those skilled in the art or by analogous methods thereto.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

Compounds of this invention may be tested for in vitro biological activity in accordance with the following assay.

Jurkat J6 Scintillation Proximity Assay (SPA)

The Jurkat J6 Scintillation Proximity Assay was used to investigate the interaction of the integrin VLA-4 (Very Late Antigen-4; α4β1; CD49d, CD29) expressed on the Jurkat J6 cell membrane with test compounds. J6 cells (1 million cells/well) were allowed to coat wheat germ agglutinin coated SPA beads (Amersham, 1 mg/well) in assay buffer containing 50 mM HEPES, 100 mM NaCl and 1 mM $MnCl_2$ (pH with 4M NaOH to 7.5). Tritiated $^3$H Standard Compound A (1-3 nM final assay concentration) and test compounds are dissolved in an appropriate solvent and diluted in assay buffer. Compounds are assayed in singlicate, a four parameter curve fit of Equation (I) being applied. The equilibrium dissociation constant for each compound was calculated according to the method of Cheng & Prusoff. Data is presented as a pKi.

Standard compound A is (2S)-3-[4-({[4-(aminocarbonyl)-1-piperidinyl]-carbonyl}oxy)-phenyl]-2-[((2S)-4-methyl-2-{[2-(2-methylphenoxy)acetyl]amino}-pentanoyl)amino] propanoic acid potassium salt which is described in patent application WO 00/37444 (Glaxo Group Ltd. et al). Tritiated $^3$H derivatives may be prepared employing conventional methods.

$$y = \frac{a-d}{1+\left(\frac{x}{c}\right)^b} + d \qquad \text{Equation (I)}$$

Where a is the minimum, b is the Hill slope, c is the $IC_{50}$ and d is the maximum. (Maximum and minimum values are those compared to adhesion in the absence of compound and in the presence of the dipotassium salt of 2 mM EDTA; Sigma Chemicals, UK, Product No. ED2P). Data is presented as the mean $pIC_{50}$.

All examples prepared in accordance with this invention were tested in accordance with this procedure and were found to have a pKi≧6.5.

Compounds of formula (I) and their pharmaceutically acceptable derivatives inhibit $α_4$ integrin mediated cell adhesion and are believed to be of potential use in the treatment or prophylaxis of such conditions as rheumatoid arthritis (RA); asthma; allergic conditions such as rhinitis; adult respiratory distress syndrome; AIDS-dementia; Alzheimer's disease; cardiovascular diseases; thrombosis or harmful platelet aggregation; reocclusion following thrombolysis; reperfusion injury; skin inflammatory diseases such as psoriasis, eczema, contact dermatitis and atopic dermatitis; diabetes (e.g., insulin-dependent diabetes mellitus, autoimmune diabetes); multiple sclerosis; systemic lupus erythematosus (SLE); inflammatory bowel disease such as ulcerative colitis, Crohn's disease (regional enteritis) and pouchitis (for example, resulting after proctocolectomy and ileoanal anastomosis); diseases associated with leukocyte infiltration to the gastrointestinal tract such as Celiac disease, nontropical Sprue, enteropathy associated with seronegative arthropathies, lymphocytic or collagenous colitis, and eosinophilic gastroenteritis; diseases associated with leukocyte infiltration to other epithelial lined tissues, such as skin, urinary tract, respiratory airway, and joint synovium; pancreatitis; mastitis (mammary gland); hepatitis; cholecystitis; cholangitis or pericholangitis (bile duct and surrounding tissue of the liver); bronchitis; sinusitis; inflammatory diseases of the lung which result in interstitial fibrosis, such as hypersensitivity pneumonitis; collagen disease (in SLE and RA); sarcoidosis; osteoporosis; osteoarthritis; atherosclerosis; neoplastic diseases including metastasis of neoplastic or cancerous growth; wound (wound healing enhancement); certain eye diseases such as retinal detachment, allergic conjunctivitis and autoimmune uveitis; Sjogren's syndrome; rejection (chronic and acute) after organ transplantation; host vs. graft or graft vs. host diseases; intimal hyperplasia; arteriosclerosis (including graft arteriosclerosis after transplantation); reinfarction or restenosis after surgery such as percutaneous transluminal coronary angioplasty (PTCA) and percutaneous transluminal artery recanalization; nephritis; tumor angiogenesis; malignant tumor; multiple myeloma and myeloma-induced bone resorption; sepsis; and central nervous system injury such as stroke, traumatic brain injury and spinal cord injury and Meniere's disease.

The compounds of the present invention can be preferably used for the treatment or prevention of asthma, allergic conditions such as rhinitis, inflammatory bowel disease such as ulcerative colitis and Crohn's disease, rheumatoid arthritis, atopic dermatitis, multiple sclerosis and rejection after organ transplantation.

The present invention further provides a method for the treatment or prophylaxis of conditions in which an inhibitor of $α_4$ mediated cell adhesion is beneficial which comprises administering to a patient in need thereof a safe and effective amount of a compound of formula (I). The present invention especially provides a method for the treatment or prophylaxis of the aforementioned conditions.

The present invention also provides a compound of formula (I) or a pharmaceutically acceptable derivative thereof for use in therapy, particularly the treatment of the aforementioned disorders.

In another aspect, the invention provides the use of a compound of formula (I) or a pharmaceutically acceptable derivative in the manufacture of a medicament for the treatment or prophylaxis of conditions in which an inhibitor of $\alpha_4$ mediated cell adhesion is beneficial, particularly the aforementioned disorders.

While it is possible for the compounds of the present invention to be administered alone, it is preferable to formulate into a pharmaceutical composition in accordance with standard pharmaceutical practice. Thus the invention also provides a pharmaceutical composition which comprises a therapeutically effective amount of a compound of formula (I) in admixture with a pharmaceutically acceptable carrier or diluent.

There is further provided by the present invention a process of preparing a pharmaceutical composition, which process comprises mixing at least one compound of the invention or a pharmaceutically acceptable derivative thereof, together with a pharmaceutically acceptable carrier or diluent.

The pharmaceutical compositions may be for human or animal usage in human and veterinary medicine and will typically comprise any one or more of a pharmaceutically acceptable diluent, carrier or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The carrier or diluent must be acceptable in the sense of being not deleterious to the recipient thereof. The pharmaceutically acceptable carrier or diluent may be, for example, binders (e.g., syrup, gum arabic, gelatin, sorbitol, tragacanth, polyvinylpyrrolidone), excipients (e.g., lactose, sucrose, corn starch, potassium phosphate, sorbitol, glycine), lubricants (e.g., magnesium stearate, talc, polyethylene glycol, silica) disintegrators (e.g., potato starch), wetting agents (e.g., sodium laurylsulfate), and the like.

The routes for administration (delivery) of the composition of the invention include, but are not limited to, one or more of: oral (e.g. as a tablet, capsule, or as an ingestible solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural, sublingual.

For example, the compound can be administered orally in the form of tablets, capsules, ovules, elixirs, solutions or suspensions, which may contain flavouring or colouring agents, for immediate-, delayed-, modified-, sustained-, pulsed- or controlled-release applications. The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent; and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the compound of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134AT"") or 1,1,1,2,3,3,3-heptafluoropropane (HFA 227EA) (for example from Inneos Fluor), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the compound and a suitable powder base such as lactose or starch.

Alternatively, the compound of the present invention can be administered in the form of a suppository or pessary, or it may be applied topically in the form of a gel, hydrogel, lotion, solution, cream, ointment or dusting powder. The compound of the present invention may also be dermally or transdermally administered, for example, by the use of a skin patch.

They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compositions of the present invention may be administered by direct injection.

In a preferred embodiment, the agents of the present invention are delivered systemically (such as orally, buccally, sublingually), more preferably orally.

Hence, preferably the agent is in a form that is suitable for oral delivery.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses.

A proposed dose of the compounds according to the present invention for administration to a human (of approximately 70 kg body weight) is 0.1 mg to 1 g, preferably 1 mg to 500 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The dosage will also depend on the route of administration. The precise dose and route of administration will ultimately be at the discretion of the attendant physician or veterinarian.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. Examples of other active agents that may be combined with a compound of formula (I) include, but not limited to: (a) other VLA-4 antagonists; (b) H1 histamine antagonists; (c) NSAID's; (d) anti-diabetic agent e.g. glitazones (e) anti-cholinergic agents (f) COX-2 inhibitors; (g) PDE-IV inhibitors; (h) steroids e.g. corticosteroids; (i) beta agonists; (j) antagonists of the chemokine receptors e.g. CCR-2, CCR-3, CCR-5 and CCR-8; (k) suitable multiple sclerosis agents such as interferon; and (l) LFA-1 antagonists.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route. When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

All publications, including but not limited to patents and patent applications, cited in this specification are herein incorporated by reference as if each individual publication were specifically and individually indicated to be incorporated by reference herein as though fully set forth.

The following Preparations and Examples illustrate the preparation of compounds of the invention.

PREPARATION 1

3-(4-Nitrophenyl)pyridine (P1)

1,1'-Bis(diphenylphosphino)ferrocenedichloropalladium (II) (0.2 g, 0.2 mmol) was added to a stirred and degassed solution of 4-bromonitrobenzene (5 g, 24.8 mmol) and pyridine-3-boronic acid (3.4 g, 27.2 mmol) in dimethyl formamide (50 mL) and 2N sodium carbonate solution in water (20 mL). The reaction mixture was stirred at 100° C. for 18 hours, then allowed to cool. The solution was filtered through celite (Diatomaceous Earth), then ethyl acetate (200 mL) was added and the organic phase was washed three time with brine (200 mL). The organic was dried (anhydrous magnesium sulfate), concentrated and purified by chromatography on silica gel (30% v/v ethyl acetate in petroleum ether) to afford the title compound as a solid.

PREPARATION 2

3-(4-Nitrophenyl)pyridine-1-oxide (P2)

m-Chloroperbenzoic acid (6.9 g, 40.0 mmol) was slowly added to a solution of 3-(4-nitrophenyl)pyridine (P1, 4 g, 20.0 mmol) in tetrahydrofuran (200 mL) and the reaction mixture was stirred at room temperature for 1 hour. The solution was poured into aqueous sodium thiosulfate and the resultant mixture was concentrated. Trituration with ethyl acetate afforded the title compound as a solid.

PREPARATION 3

3-(4-Nitrophenyl)-1H-pyridin-2-one (P3)

3-(4-Nitrophenyl)pyridine-1-oxide (P2, 2.5 g, 11.6 mmol) was stirred at reflux in acetic anhydride (25 mL) for 18 hours, then allowed to cool. The reaction mixture was concentrated and concentrated hydrochloric acid (25 mL) was added. The solution was stirred at reflux for 4 hours, then allowed to cool. The reaction mixture was poured onto ice/water and filtration followed by drying under high vacuum afforded the title compound as a solid.

PREPARATION 4

3-(4-Hydroxymethylphenyl)acrylic acid ethyl ester (P4)

4-Bromobenzyl alcohol (10.5 g, 56.1 mmol), triphenylphosphine (0.5 g, 1.9 mmol) and palladium acetate (0.5 g, 2.2 mmol) were stirred at reflux in ethyl acrylate (20 mL) and triethylamine (100 mL) for 72 hours, then allowed to cool. The reaction mixture was filtered through celite (Diatomaceous Earth), then concentrated. The crude solid was purified by chromatography on silica gel (20% v/v ethyl acetate in petroleum ether) to afford the title compound as an oil.

PREPARATION 5

3-(4-Hydroxymethylphenyl)propionic acid ethyl ester (P5)

3-(4-Hydroxymethylphenyl)acrylic acid ethyl ester (P4, 3 g, 14.5 mmol) and palladium on charcoal (0.3 g) in ethanol (30 mL) was stirred for 4 hours under atmospheric pressure of hydrogen. The reaction mixture was filtered through celite (Diatomaceous Earth) and concentrated to afford the title compound as an oil.

PREPARATION 6

3-(4-Chloromethylphenyl)propionic acid ethyl ester (P6)

To a stirred solution of 3-(4-hydroxymethylphenyl)propionic acid ethyl ester (P5, 2.9 g, 13.9 mmol) in triethylamine (4.0 mL, 27.8 mmol) and dichloromethane (30 mL) was slowly added at 0° C. mesyl chloride (1.6 mL, 20.9 mmol). The solution was stirred at room temperature for 18 hours, then the solution was washed with 1N aqueous hydrochloric acid. The organic phase was dried (anhydrous magnesium sulfate) and concentrated to afford the title compound as an oil.

PREPARATION 7

3-{4-[3-(4-Nitrophenyl)-2-oxo-2H-pyridin-1-ylmethyl]phenyl}propionic acid ethyl ester (P7)

3-(4-Nitrophenyl)-1H-pyridin-2-one (P3, 200 mg, 0.93 mmol), 3-(4-chloromethyl-phenyl)propionic acid ethyl ester (P6, 270 mg, 1.20 mmol) and cesium carbonate (900 mg, 2.78 mmol) were stirred for 18 hours in dimethyl formamide (5 mL) at room temperature. The reaction mixture was filtered through celite (Diatomaceous Earth), concentrated and the crude mixture was purified by chromatography on silica gel (50% v/v ethyl acetate in petroleum ether) to afford the title compound as a solid.

PREPARATION 8

3-{4-[3-(4-Aminophenyl)-2-oxo-2H-pyridin-1-ylmethyl]phenyl}propionic acid ethyl ester (P8)

3-{4-[3-(4-Nitrophenyl)-2-oxo-2H-pyridin-1-ylmethyl]phenyl}propionic acid ethyl ester (P7, 300 mg, 0.74 mmol) and palladium on charcoal (30 mg) were stirred at room temperature in ethanol (10 mL) under atmospheric pressure of hydrogen for 3 hours, then the reaction mixture was filtered through celite and concentrated. The crude oil was purified by chromatography on silica gel (50% v/v ethyl acetate in petroleum ether) to afford the title compound as an oil.

PREPARATION 9

3-(4-{2-Oxo-3-[4-(3-o-tolyl-ureido)phenyl]-2H-pyridin-1-ylmethyl}phenyl)-propionic acid ethyl ester (P9)

3-{4-[3-(4-Aminophenyl)-2-oxo-2H-pyridin-1-ylmethyl]phenyl}propionic acid ethyl ester (P8, 60 mg, 0.16 mmol) and o-tolyl isocyanate (40 [2 L, 0.32 mmol) were stirred at room temperature in dichloromethane (5 mL) for 3 hours, then the reaction mixture was concentrated. Trituration with diethyl ether afforded the title compound as a solid.

PREPARATION 10

3-{4-[3-(4-Aminophenyl)-5-chloro-2-oxo-2H-pyridin-1-ylmethyl]phenyl}-propionic acid ethyl ester (P10)

Acetic acid (1 mL) followed by iron (160 mg, 2.9 mmol) were added to a solution of 3-(4-[5-chloro-3-(4-nitrophenyl)-2-oxo-2H-pyridin-1-ylmethyl]phenyl}-propionic acid ethyl ester (0.31 g, 0.72 mmol) in ethanol (10 mL) and water (5 mL) with stirring. The mixture was then heated at reflux for 2 hours and allowed to cool to room temperature. After basification with aqueous ammonia the mixture was filtered through a pad of celite (Diatomaceous Earth) and the filtrate evaporated to dryness. The residue was taken up in aqueous sodium bicarbonate/ethyl acetate and the organic layer washed with brine, dried over anhydrous sodium sulfate, filtered and evaporated to dryness. After purification by chromatography on silica gel with a gradient of 30-50% ethyl acetate in hexane the title compound was obtained as an oil.

PREPARATION 11

(±)-3-{4-[3-(4-Aminophenyl-2-oxo-2H-pyridin-1-ylmethyl]phenyl}butyric acid methyl ester (P11)

Sodium borohydride (0.042 g, 1.1 mmol) was added to a solution of nickel dichloride hexahydrate (0.088 g, 0.37 mmol) in methanol (15 mL) and the mixture stirred for 30 minutes at room temperature before adding a solution of (E)-3-{4-[3-(4-nitrophenyl)$_2$H-oxo-2-pyridin-1-yl]phenyl}but-2-enoic acid methyl ester (0.3 g, 0.74 mmol) in methanol (10 mL). A further portion of sodium borohydride (0.098 g, 2.59 mmol) was added and stirring continued overnight. A further portion of sodium borohydride (0.15 g, 3.96 mmol) was then added to take the reaction to completion. The mixture was filtered through celite, washed with methanol (50 mL) and the filtrate concentrated in vacuo. The residue was extracted with chloroform (2×50 mL) and the organic phase washed with water (20 mL) and then the organic layer dried with anhydrous magnesium sulfate, filtered and evaporated to dryness to give the title compound as an oil.

For the above synthesis, (E)-3-{4-[3-(4-nitrophenyl)-2H-oxo-2-pyridin-1-yl]phenyl}but-2-enoic acid methyl ester was prepared from P3 and (E)-3-(4-methanesulfonyloxymethylphenyl)but-2-enoic acid methyl ester by the method of Preparation 7, and (E)-3-(4-methanesulfonyloxymethylphenyl)but-2-enoic acid methyl ester was prepared from (E)-3-(4-hydroxymethylphenyl)but-2-enoic acid methyl ester and methanesulfonyl chloride analogously to the method of Preparation 6 (in this case mostly the mesylate was isolated rather than the chloride). (E)-3-(4-hydroxymethylphenyl)but-2-enoic acid methyl ester was prepared analogously to the method of Preparation 4 from 4-bromobenzyl alcohol and methyl crotonate.

PREPARATION 11a (±)-3-(4-{2-Oxo-3-[4-(3-o-tolyl-ureido)phenyl]-2H-pyridin-1-ylmethyl}-phenyl)butyric acid methyl ester (P11a)

The title compound was prepared from (±)-3-{4-[3-(4-aminophenyl-2-oxo-2H-pyridin-1-ylmethyl]phenyl}butyric acid methyl ester (P11) and o-tolyl isocyanate by the method of Preparation 9.

PREPARATION 12

1-[3-Fluoro-4-(2-methoxypyridin-3-yl)phenyl]-3-o-tolylurea (P12)

1,1'-Bis(diphenylphosphino)ferrocenedichloropalladium (II) (0.1 g) was added to a stirred and degassed solution of 1-(4-bromo-3-fluorophenyl)-3-o-tolylurea (0.5 g, 1.5 mmol) and 2-methoxypyrid-3-ylboronic acid (258 mg, 1.7 mmol) in dimethyl formamide (10 mL) and aqueous sodium carbonate in water (5 mL, 2N). The reaction mixture was stirred at 100° C. for 18 hours, then allowed to cool. The solution was concentrated, then ethyl acetate (75 mL) was added and the organic phase was washed with water (3×75 mL). The organic phase was dried (anhydrous magnesium sulfate), concentrated and purified by chromatography on silica gel (20 to 40% v/v ethyl acetate in hexane) to afford the title compound as an oil.

MS (ES+ve): [M+H]$^+$ at m/z 352 ($C_{20}H_{18}FN_3O_2$ requires [M+H]$^+$ at m/z 352).

PREPARATION 13

1-[3-Fluoro-4-(2-oxo-1,2-dihydropyridin-3-yl)phenyl]-3-o-tolylurea (P13)

1-[3-Fluoro-4-(2-methoxypyridin-3-yl)phenyl]-3-o-tolylurea (P12) (0.150 g, 0.43 mmol) in ethanolic hydrochloric acid (10 mL) was stirred at reflux for 8 hours. The reaction mixture was then allowed to cool, and concentrated to afford the title compound as a solid.

MS (ES+ve): [M+H]$^+$ at m/z 338 ($C_{19}H_{16}FN_3O_2$ requires [M+H]$^+$ at m/z 338).

PREPARATION 14

Ethyl 4-[2-((S)-2-hydroxy-1-phenylethylcarbamoyl)-1-(R,S)-methylethyl]-benzoate (P14)

To a solution of ethyl 4-(2-carboxy-1-methylethyl)benzoate (J. I. DeGraw et al. *J. Med. Chem.* 1986, 29, 1056) (3.54 g, 15 mmol) in dichloromethane (100 mL) cooled in an ice bath was added oxalyl chloride (3.9 mL, 45 mmol). Dimethylformamide (0.1 mL) was added and the mixture stirred at room temperature for 2 hours, then concentrated under reduced pressure. The residual acid chloride was dissolved in dichloromethane (60 mL) and added to an ice-cooled mixture of (S)-2-phenylglycinol (2.72 g, 20 mmol) and triethylamine (6.3 mL, 45 mmol) in dichloromethane (60 mL) over 30 minutes. The reaction mixture was stirred at room temperature for 1 hour. 2N Hydrochloric acid was added, the organic phase was separated, then washed with water, dried (anhydrous magnesium sulfate) and evaporated. The diastereomeric products were separated by flash chromatography with elution by ethyl acetate, then ethyl acetate-methanol (9:1). There were obtained an earlier eluting (SS) diastereomer (P14a); TLC (silica gel; ethyl acetate) R$_f$ 0.36; MS (ES+ve): [M+H]$^+$ at m/z 356 ($C_{21}H_{25}NO_4$ requires [M+H]$^+$ at m/z 356); and a later eluting (RS) diastereomer (P14b); TLC (silica gel; ethyl acetate) R$_f$ 0.19; MS (ES+ve): [M+H]$^+$ at m/z 356 ($C_{21}H_{25}NO_4$ requires [M+H]$^+$ at m/z 356).

PREPARATION 15

3-(R and S)-(4-Hydroxymethylphenyl)-N-((S)-2-hydroxy-1-phenylethyl)-butyramide (P15a and P15b)

To a solution of the later eluting diastereomer (P14b) (2.42 g, 6.81 mmol) in tetrahydrofuran (100 mL) was added a solution of lithium borohydride in tetrahydrofuran (2M, 15 mL, 30 mmol). Methanol (1 mL) was added dropwise and the reaction mixture stirred at room temperature for 2 hours. A further portion of lithium borohydride in tetrahydrofuran (2M, 10 mL, 20 mmol) and methanol (0.8 mL) were added and the mixture stirred for a further 3 hours, then cooled in an ice bath. 2M Hydrochloric acid (100 mL) was added cautiously, then the mixture was concentrated under reduced pressure. Ethyl acetate was added and the organic phase washed with water, then brine, dried (anhydrous magnesium sulfate) and evaporated to give the (RS) diastereomer (P15b) of the title compound;

MS (ES−ve): [M−H]$^-$ at m/z 312 ($C_{19}H_{23}NO_3$ requires [M−H]$^-$ at m/z 312).

The (SS) diastereomer (P15a) was prepared in a similar manner from the earlier eluting diastereomer P14a.

PREPARATION 16

Methyl (R)-(−)-3-(4-hydroxymethylphenyl)butyrate (P16)

To a solution of the diastereomer P15b (2.0 g, 6.38 mmol) in dioxane (85 mL) was added 3N sulphuric acid (85 mL). The mixture was heated at reflux for 6 hours, cooled and then concentrated under reduced pressure. The concentrate was extracted three times with ethyl acetate, the combined organic phases were washed with water, then brine, dried (anhydrous magnesium sulfate) and evaporated. The residual solid was dissolved in methanol (90 mL) and concentrated sulphuric acid (2 mL) added. The mixture was refluxed for 1 hour, cooled and then concentrated under reduced pressure. Water and ethyl acetate were added and the organic phase was washed with water, then brine, dried (anhydrous magnesium sulfate) and evaporated. Purification by flash chromatography with elution by ethyl acetate-hexane (1:1) gave the title compound as a colourless oil; $[\alpha]_D^{30°\,C.}$ −41.2° (c=1.0, MeOH).

PREPARATION 17

Methyl (S)-(+)-3-(4-hydroxymethylphenyl)butyrate (P17)

The title compound was prepared from the diastereomer P15a in a similar manner to that of Preparation 16; $[\alpha]_D^{30°\,C.}$ +42.4° (c=1.0, MeOH).

PREPARATION 18

Methyl (R)-(−)-3-(4-{2-oxo-3-[4-(3-o-tolylureido)phenyl]-2H-pyridin-1-ylmethyl}-phenyl)butyrate (P18)

To a solution of the product from step P16 (0.4 g, 1.92 mmol) in dichloromethane at 0° C. was added triethylamine (0.3 mL, 0.22 mmol), then methanesulfonyl chloride (0.16 mL, 2.1 mmol). The mixture was stirred at 0° C. for 2 hours, then washed with water, dried (anhydrous magnesium sulfate) and evaporated. The resulting mesylate was dissolved in dimethyl formamide (20 mL), and 1-[4-(2-oxo-1,2-dihydropyridin-3-yl)phenyl]-3-o-tolylurea (0.612 g, 1.92 mmol) and cesium carbonate (1.25 g, 3.84 mmol) were added. The mixture was stirred at room temperature for 3 hours and then concentrated under reduced pressure. The residue was partitioned between ethyl acetate and water and the organic phase was washed with water, then brine, dried (anhydrous magnesium sulfate) and evaporated. Purification by flash chromatography with elution by ethyl acetate-toluene mixtures gave the title compound as a colourless gum; $[\alpha]_D^{26° \text{ C.}} -17.2°$ (c=0.5, MeOH); MS (ES+ve): [M+H]$^+$ at m/z 510 ($C_{31}H_{31}N_3O_4$ requires [M+H]$^+$ at m/z 510).

PREPARATION 19

Methyl (S)-(+)-3-(4-{2-oxo-3-[4-(3-o-tolylureido) phenyl]-2H-pyridin-1-ylmethyl}phenyl) butyrate (P19)

The title compound was prepared from P17 in a similar manner to the preparation of P18; $[\alpha]_D^{30° \text{ C.}} +17.0°$ (c=0.5, MeOH); MS (ES+ve): [M+H]$^+$ at m/z 510 ($C_{31}H_{31}N_3O_4$ requires [M+H]$^+$ at m/z 510).

PREPARATION 20

4-[2-Ethoxycarbonylethyl]phenylboronic acid (P20)

4-(2-Carboxyethyl)phenylboronic acid (4 g, 20.6 mmol) was stirred at reflux for 24 hours in ethanolic hydrochloric acid. The reaction mixture was cooled, then concentrated to afford the title compound as an oil.

PREPARATION 21

3-(4-Pyridin-3-yl-phenyl)propionic acid ethyl ester (P21)

1,1'-Bis(diphenylphosphino)ferrocenedichloropalladium (II) (0.1 g, 0.1 mmol) was added to a stirred and degassed solution of 3-bromopyridine (1.5 ml, 15.6 mmol) and 4-[2-ethoxycarbonylethyl]phenylboronic acid (P20) (3.5 g, 15.8 mmol) in dimethyl formamide (30 mL) and 2N sodium carbonate solution in water (15 mL). The reaction mixture was stirred at 100° C. for 18 hours, then allowed to cool. The solution was filtered through celite, then ethyl acetate (100 mL) was added and the organic phase was washed three times with brine (100 mL). The organic layer was dried (anhydrous magnesium sulfate), concentrated and purified by chromatography on silica gel (30% v/v ethyl acetate in petroleum ether) to afford the title compound as an oil.

PREPARATION 22

3-[4-(3-{4-[(1-2,3-Dihydroindol-1-ylmethanoyl) amino]phenyl}-2-oxo-2H-pyridin-1-ylmethyl)phenyl]propionic acid methyl ester (P22)

A solution of 3-{4-[3-(4-aminophenyl)-2-oxo-2H-pyridin-1-ylmethyl]phenyl}propionic acid methyl ester in tetrahydrofuran (5 mL) was added to a stirred solution of triphosgene (0.135 g, 0.45 mmol) in tetrahydrofuran (5 mL) at 0° C. After 2 hours a solution of indoline (0.054 g, 0.45 mmol) in tetrahydrofuran (2.5 mL) was added and stirring continued at room temperature for 18 hours. The mixture was then poured into ethyl acetate (25 mL) and washed sequentially with hydrochloric acid (10 mL, 1M), saturated aqueous sodium bicarbonate (10 mL) and brine before drying over anhydrous magnesium sulfate. After filtration and evaporation to dryness the residue was chromatographed on silica gel with a gradient of 1:1 rising to 3:1 ethyl acetate to hexane to give the title compound as a solid.

PREPARATION 23

(±)-3-(3-{2-Oxo-3-[4-(3-o-tolyl-ureido)phenyl]piperidin-1-ylmethyl}phenyl)-propionic acid ethyl ester (P23)

(E)-3-{3-[3-(4-Nitrophenyl-2-oxo-2H-pyridin-1-ylmethyl]phenyl}acrytic acid ethyl ester (85 mg, 0.21 mmol) with 10% palladium on charcoal in ethanol (20 mL) was hydrogenated at atmospheric pressure for 18 hours. The reaction mixture was then filtered through celite, evaporated to dryness and purified by chromatography on silica gel with 70% ethyl acetate/petroleum ether to give the title compound as an oil.

MS (AP+ve): [M+H]$^+$ at m/z 381 ($C_{23}H_{28}N_2O_3$ requires [M+H]$^+$ at m/z 381).

PREPARATION 24

3-{4-[3-(4-Nitrophenyl)-2-oxo-2H-pyridin-1-yl] phenyl}propionic acid ethyl ester (P24)

3-(4-Nitrophenyl)-1H-pyridin-2-one (P3) (0.2 g, 0.92 mmol), copper (II) acetate (0.334 g, 2 equiv.), diisopropylethylamine (0.31 mL, 2 equiv.), and pyridine (0.15 mL, 2 equiv.) were added to a stirred solution of 4-(2-ethoxycarbonylethyl)phenyl boronic acid (0.308 g, 1.3 mmol) in dichloromethane (10 mL). The reaction mixture was then stirred under argon at room temperature for 4 hours. The solution was then filtered through celite, concentrated and purified by chromatography on silica gel (50% v/v ethyl acetate in hexane) to afford the title compound as an oil.

MS (ES+ve): [M+H]$^+$ at m/z 393 ($C_{22}H_{20}N_2O_5$ requires [M+H]$^+$ at m/z 393).

EXAMPLE 1

3-(4-{2-Oxo-3-[4-(3-o-tolyl-ureido)phenyl]-2H-pyridin-1-ylmethyl}phenyl)-propionic acid (E1)

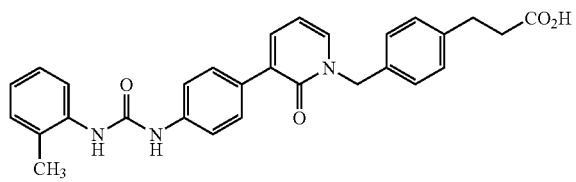

3-(4-{2-Oxo-3-[4-(3-o-tolyl-ureido)phenyl]2H-pyridin-1-ylmethyl}phenyl)propionic acid ethyl ester (P9, 55 mg, 0.11 mmol) and lithium hydroxide (50 mg, 2.5 mmol) were stirred at 60° C. for 30 minutes in tetrahydrofuran (5 mL) and water (5 mL). The reaction mixture was acidified to pH 1 with 1 N aqueous hydrochloric acid and extracted with ethyl acetate. The organic layer was dried (anhydrous magnesium sulfate) and evaporated to dryness to afford the title compound as a solid.

$^1$H NMR δ (DMSO-d6): 2.21-2.27 (5H, m), 2.73-2.80 (2H, t), 5.12 (2H, s), 6.28-6.34 (1H, t), 6.89-6.95 (1H, m), 7.12-7.25 (6H, m), 7.51-7.63 (5H, m), 7.68-7.77 (2H, m), 9.28 (1H, s), 10.47 (1H, s).

MS (APCI-ve): [M]$^-$ at m/z 481, [M–H]$^-$ at m/z 480 ($C_{29}H_{27}N_3O_4$ requires [M–H]$^-$ at m/z 480).

EXAMPLE 2

3-(3-{2-Oxo-3-[4-(3-o-tolyl-ureido)phenyl]-2H-pyridin-1-ylmethyl}phenyl)-propionic acid (E2)

The title compound was prepared using an analogous procedure to that of Example 1.

MS (ES+ve): $[M+H]^+$ at m/z 482 ($C_{29}H_{27}N_3O_4$ requires $[M+H]^+$ at m/z 482).

Unless otherwise stated the Examples listed in Table 1 were prepared in an analogous manner to that of Example 1. Variations from this procedure are described below for Examples E7, E9, E11, E23, E30, E31, E32, E34 and E35.

TABLE 1

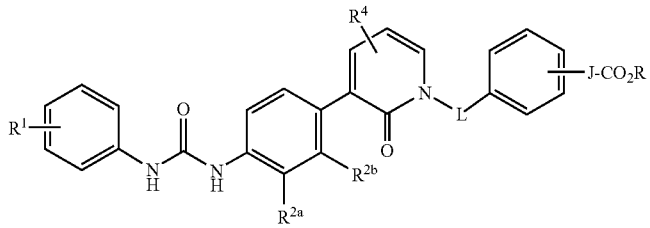

| Ex. | $R^1$ | $R^{2a}$ | $R^{2b}$ | $R^4$ | L | $J$-$CO_2R$ | Observed* $[M + H]^+$ or $[M - H]^-$ or $M^-$ |
|---|---|---|---|---|---|---|---|
| E3  | 2-Me      | H   | H | H    | $CH_2$     | 4-OCH$_2$CO$_2$H | 484 |
| E4  | 2-Me      | H   | H | H    | $(CH_2)_2$ | 4-CO$_2$H | 468 |
| E5  | 2-Me      | OMe | H | H    | $CH_2$     | 4-(CH$_2$)$_2$CO$_2$H | 512 |
| E6  | 2-Me      | H   | H | H    | $CH_2$     | 3-OCH$_2$CO$_2$H | 484 |
| E7  | 2-Me      | H   | H | 5-Cl | $CH_2$     | 4-(CH$_2$)$_2$CO$_2$H | 516 |
| E8  | 2-Me      | H   | H | H    | $CH_2$     | 4-CO$_2$H | 454 |
| E9  | 2-Me      | H   | H | H    | $CH_2$     | (±)-4-CH(Me)CH$_2$CO$_2$H | 496 |
| E10 | 2-Me      | H   | H | H    | $CH_2$     | (±)-3-CH(Me)CH$_2$CO$_2$H | 496 |
| E11 | 2-Me      | H   | H | H    | $CH_2$     | 4-NMeCH$_2$CO$_2$H | 497 |
| E12 | 2-Me      | OMe | H | H    | $CH_2$     | (±)-4-CH(Me)CH$_2$CO$_2$H | 526 |
| E13 | 2-Me      | H   | H | H    | $CH_2$     | 4-(CH$_2$)$_2$CO$_2$Me | 496 |
| E14 | 2-Me      | H   | H | H    | $CH_2$     | 3-NMeCH$_2$CO$_2$H | 497 |
| E15 | 2-Me      | H   | H | H    | $CH_2$     | 4-(CH$_2$)$_2$CO$_2$Et | 510 |
| E16 | 2-Me      | H   | H | H    | $(CH_2)_2O$ | 4-CO$_2$H | $[M - H]^-$ 482 |
| E17 | 2-Me      | H   | H | H    | $CH_2$     | 4-(CH$_2$)$_2$CO$_2$CH$_2$OCO$_2$cyc-Hex | 638 |
| E18 | 2-Me      | H   | H | H    | $CH_2$     | 4-(CH$_2$)$_2$CO$_2$CH$_2$OCO$_2$iso-Pr | 598 |
| E19 | 2-Me      | H   | H | H    | $CH_2$     | 4-(CH$_2$)$_2$CO$_2$CH$_2$OAc | 554 |
| E20 | 2-Me      | H   | H | H    | $CH_2$     | 4-(CH$_2$)$_2$CO$_2$iso-Pr | 524 |
| E21 | 2-Me      | H   | H | H    | $(CH_2)_2$ | 3-CH$_2$CO$_2$H | 482 |
| E22 | 2-Me      | H   | H | H    | $(CH_2)_2$ | 4-CH$_2$CO$_2$H | 482 |
| E23 | 2-Me      | H   | H | H    | $CH_2$     | (±)-4-CH$_2$CH(NHAc)CO$_2$H | 539 |
| E24 | 2-Me      | H   | H | H    | $CH_2$     | 3-CH$_2$CO$_2$H | 468 |
| E25 | 2-F       | OMe | H | H    | $CH_2$     | 4-(CH$_2$)$_2$CO$_2$H | 516 |
| E26 | H         | H   | H | H    | $CH_2$     | 4-(CH$_2$)$_2$CO$_2$H | $[M - H]^-$ 466 |
| E27 | 2-F       | H   | H | H    | $CH_2$     | 4-(CH$_2$)$_2$CO$_2$H | 486 |
| E28 | 2,3-diF   | H   | H | H    | $CH_2$     | 4-(CH$_2$)$_2$CO$_2$H | 504 |
| E29 | 2-Me-3-F  | H   | H | H    | $CH_2$     | 4-(CH$_2$)$_2$CO$_2$H | 500 |
| E30 | 2-Me      | H   | F | H    | $CH_2$     | 4-(CH$_2$)$_2$CO$_2$H | 500 |
| E31 | 2-Me      | H   | H | H    | $CH_2$     | (S)-(+)-4-CH(Me)CH$_2$CO$_2$H | 496 |
| E32 | 2-Me      | H   | H | H    | $CH_2$     | (R)-(−)-4-CH(Me)CH$_2$CO$_2$H | 496 |
| E33 | 2-Me      | H   | H | H    | $CH_2$     | (±)-4-CH(Ph)CH$_2$CO$_2$H | 558 |
| E34 | 2-Me      | H   | H | H    | $CH_2$     | (S)-(+)-4-CH(Et)CH$_2$CO$_2$H | 510 |
| E35 | 2-Me      | H   | H | H    | $CH_2$     | (R)-(−)-4-CH(Et)CH$_2$CO$_2$H | 510 |
| E36 | 2-Me      | H   | H | H    | $CH_2$     | 4-C(Me)$_2$CH$_2$CO$_2$H | 510 |
| E37 | 2-Me      | H   | H | H    | $CH_2$     | 4-[(1-CH$_2$CO$_2$H)-cyc-pent-1-yl] | |

*$[M + H]^+$ unless indicated otherwise

EXAMPLE 7

3-(4-{5-Chloro-2-oxo-3-[4-(3-o-tolyl-ureido)phenyl]-2H-pyridin-1-ylmethyl}-phenyl)propionic acid (E7)

The title compound was prepared analogously to Example 1 with the additional step of chlorine introduction. 3-(4-Nitrophenyl)-1H-pyridin-2-one (P3) is treated with N-chlorosuccinimide by a similar procedure to that of Imming et al., European J. Med. Chem. 2001, 36(4), 375, to give 5-chloro-3-(4-nitrophenyl)-1H-pyrid-2-one. An additional modification in the preparation of Example 7 is that the nitro group is reduced by the method of Preparation 10.

EXAMPLE 9

(±)-3-(4-{2-Oxo-3-[4-(3-o-tolyl-ureido)phenyl]-2H-pyridin-1-ylmethyl}phenyl)-butyric acid (E9)

(±)-3-(4-{2-Oxo-3-[4-(3-o-tolyl-ureido)phenyl]-2H-pyridin-1-ylmethyl}phenyl)-butyric acid methyl ester (0.21 g, 0.41 mmol) was dissolved in tetrahydrofuran (3 mL) and aqueous lithium hydroxide (0.5 M, 3 mL) added with stirring. The mixture was heated at 65° C. for 2 hours and then allowed to cool and concentrated in vacuo. The mixture was acidified with hydrochloric acid (2M), extracted with ethyl acetate (2×25 mL) and the combined organic layers washed with brine and dried over anhydrous magnesium sulfate. After filtration and evaporation to dryness the title compound was obtained as a white solid.

$^1$H NMR δ (DMSO-$d_6$): 11.92 (1H, br s), 9.08 (1H, s), 7.92 (1H, s), 7.85 (1H, d), 7.80 (1H, dd), 7.65 (2H, d), 7.59 (2H, d), 7.27 (2H, d), 7.22 (2H, d), 7.10-7.20 (2H, m), 6.94 (1H, t), 6.34 (1H, t), 5.14 (2H, s), 3.11 (1H, m), 2.25 (3H, s), 1.18 (3H, d)

EXAMPLE 11

[Methyl-(4-{2-oxo-3-[4-(3-o-tolyl-ureido)phenyl]-2H-pyridin-1-ylmethyl}-phenyl)amino]acetic acid (E11)

Potassium trimethylsilanolate (0.035 g, 0.25 mmol) was added to a solution of [methyl-(4-{2-oxo-3-[4-(3-o-tolyl-ureido)phenyl]-2H-pyridin-1-ylmethyl}phenyl)amino]acetic acid ethyl ester (0.90 g, 0.17 mmol) in tetrahydrofuran (5 mL) and the mixture stirred at room temperature for 2 hours. A solution of hydrochloric acid in diethyl ether (1 M, 1 mL) was added and solvent evaporated. The residue was triturated with diethyl ether, filtered and dried to give the title compound as a solid.

$^1$H NMR δ (DMSO-$d_6$): 9.35 (1H, s), 8.10 (1H, s), 7.85 (1H, d), 7.75 (1H, dd), 7.65 (2H, d), 7.55 (1H, dd), 7.47 (2H, d), 7.22 (2H, d), 7.10-7.20 (2H, m), 6.94 (1H, t), 6.61 (2H, d), 6.30 (1H, t), 5.03 (2H, s), 4.06 (2H, s), 2.94 (3H, s), 2.26 (3H, s)

The compound [methyl-(4-{2-oxo-3-[4-(3-o-tolyl-ureido)phenyl]-2H-pyridin-1-ylmethyl}phenyl)amino]acetic acid ethyl ester was prepared by a method as shown in Reaction Scheme 1.

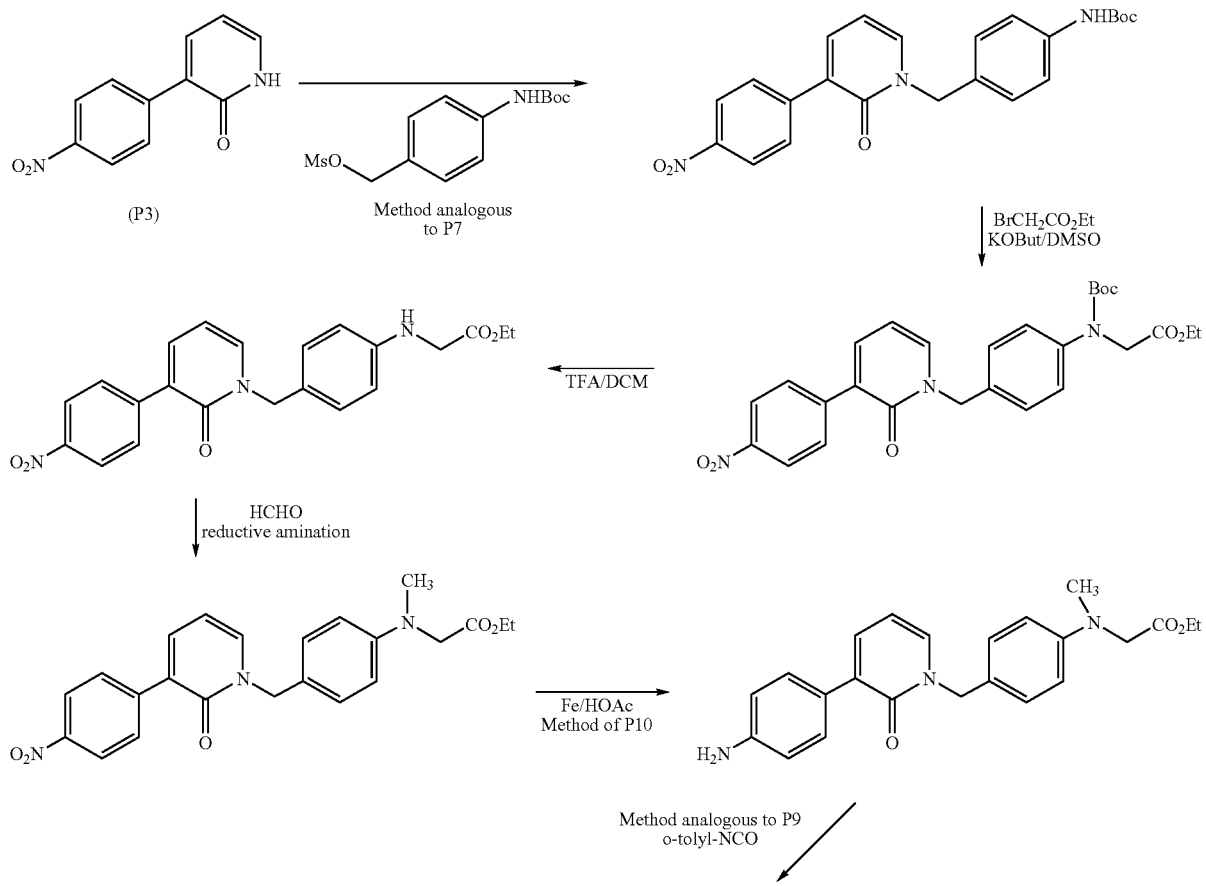

Reaction Scheme 1

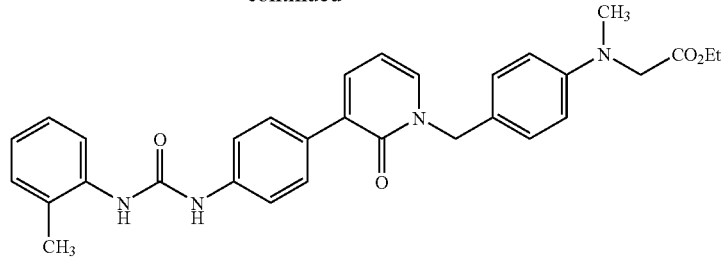

EXAMPLE 23

2-Acetylamino-3-(4-{2-oxo-3-[4-(3-o-tolyl-ureido)phenyl]-2H-pyridin-1-ylmethyl}phenyl)propionic acid (E23)

The title compound was prepared by standard procedures described herein, the alkylating agent being prepared from the alcohol resulting from the coupling of 4-bromobenzyl alcohol and methyl 2-methylacetamidoacrylate by a procedure analogous to Preparation 4.

EXAMPLE 30

3-(4-{3-[2-Fluoro-4-(3-o-tolyl-ureido)phenyl]-2-oxo-2H-pyridin-1-ylmethyl}-phenyl)propionic acid (E30)

The title compound was prepared following the method of Preparations 12 and 13 with subsequent alkylation by the procedure of Preparation 7 and hydrolysis by the general method of Example 1.

EXAMPLE 31

(S)-(+)-3-(4-{2-Oxo-3-[4-(3-o-tolylureido)phenyl]-2H-pyridin-1-ylmethyl}-phenyl)butyric acid (E31)

The title compound was prepared from P19 in a similar manner to that of Example 32; $[\alpha]_D^{30°\ C.}$+14.0° (c=0.5, MeOH); MS (ES+ve): [M+H]$^+$ at m/z 496 ($C_{30}H_{29}N_3O_4$ requires [M+H]$^+$ at m/z 496).

EXAMPLE 32

(R)-(−)-3-(4-{2-Oxo-3-[4-(3-o-tolylureido)phenyl]-2H-pyridin-1-ylmethyl}-phenyl)butyric acid (E32)

To a solution of P18 (1.02 g, 2.0 mmol) in tetrahydrofuran (40 mL) was added a solution of lithium hydroxide in water (0.5M, 40 mL, 20 mmol). The mixture was stirred at room temperature for 3 hours and then concentrated. Ethyl acetate was added and the mixture was acidified by the addition of 2N hydrochloric acid. The organic phase was washed with water, then brine, dried (anhydrous magnesium sulfate) and evaporated. Trituration with diethyl ether gave the title compound as a white solid; $[\alpha]_D^{30°\ C.}$−14.2° (c=0.5, MeOH); MS (ES+ve): [M+H]$^+$ at m/z 496 ($C_{30}H_{29}N_3O_4$ requires [M+H]$^+$ at m/z 496).

The chiral ethyl substituted analogues E34 and E35 were prepared analogously to the corresponding methyl analogues E31 and E32. The required precursor, 4-(1-carboxymethylpropyl)benzoic acid methyl ester, was prepared in 4 steps from 4-hydroxypropiophenone by standard procedures (formation of the corresponding triflate, carbonylation with palladium acetate in the presence of methanol to give the methyl ester, Wittig reaction with the anion of dimethyl(benzyloxycarbonyl)methylphosphonate to give a mixture of unsaturated benzyl esters, which were hydrogenated to give the required saturated acid).

EXAMPLE 38

3-(4-{2-Oxo-1-[4-(3-o-tolyl-ureido)benzyl]-1,2-dihydropyridin-3-yl}phenyl)-propionic acid (E38)

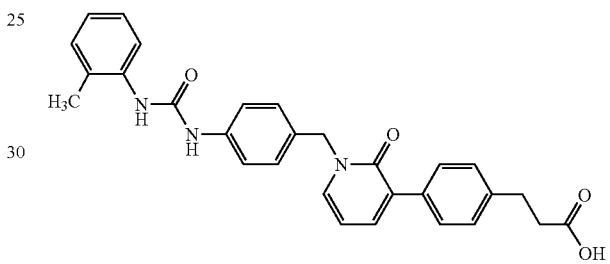

The procedures used to prepare the title compound are analogous to the those described for Example 1 and associated Preparations with the intermediate pyridine, 3-(4-pyridin-3-yl-phenyl)propionic acid ethyl ester, being prepared by the methods of Preparations 20 and 21. Subsequent oxidation and rearrangement to the required pyridone affords a convenient precursor for alkylation. Subsequent hydrolysis by the method of Example 1 affords the title compound as a solid.

MS (APCI+ve): [M+H]$^+$ at m/z 482 ($C_{29}H_{27}N_3O_4$ requires [M+H]$^+$ at m/z 482)

EXAMPLE 39

3-[4-(3-{4-[(1-2,3-Dihydroindol-1-yl-methanoyl)amino]phenyl}-2-oxo-2H-pyridin-1-ylmethyl)phenyl]propionic acid (E39)

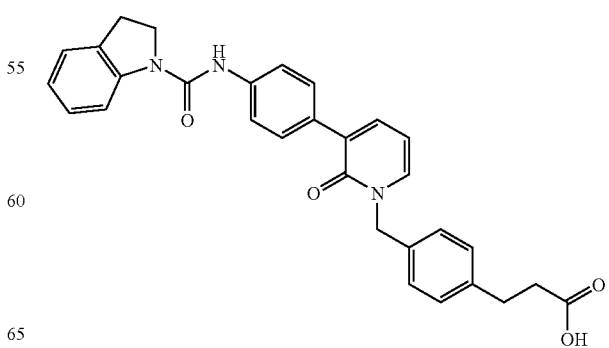

The title compound was prepared from the corresponding methyl ester (P22) by the method of Example 1 to give the title compound as a solid.

MS (ES+ve): [M+H]$^+$ at m/z 494 (C$_{30}$H$_{27}$N$_3$O$_4$ requires [M+H]$^+$ at m/z 494).

EXAMPLE 40

3-{4-[2'-Oxo-5-(3tolyl-ureido)-2'H-[2,3']bipyridinyl-1'-ylmethyl]-phenyl}propionic acid (E40)

The title compound was prepared by a method as shown in Reaction Scheme 2.

MS (ES+ve): [M+H]$^+$ at m/z 483 (C$_{28}$H$_{26}$N$_4$O$_4$ requires [M+H]$^+$ at m/z 483)

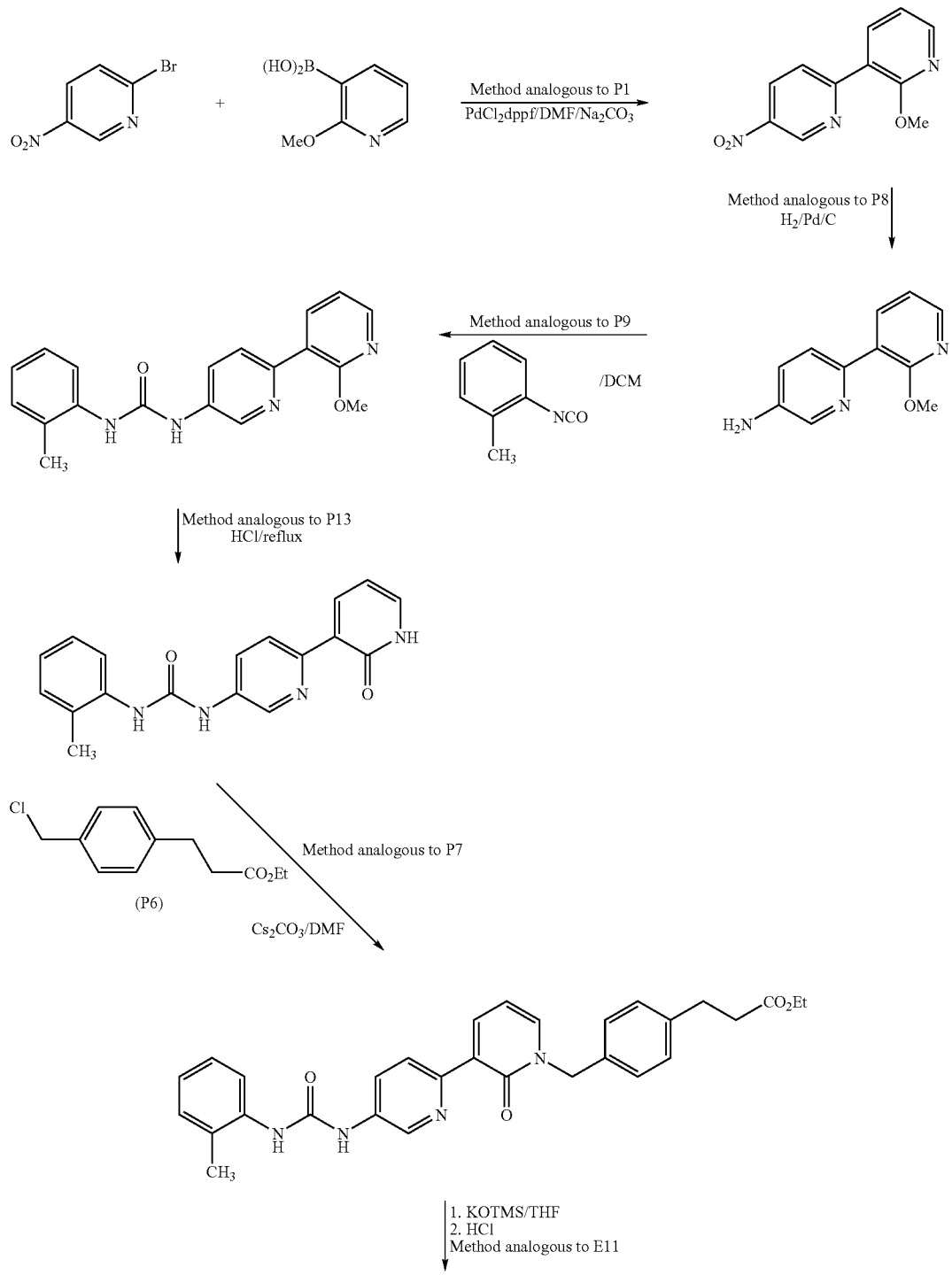

Reaction Scheme 2

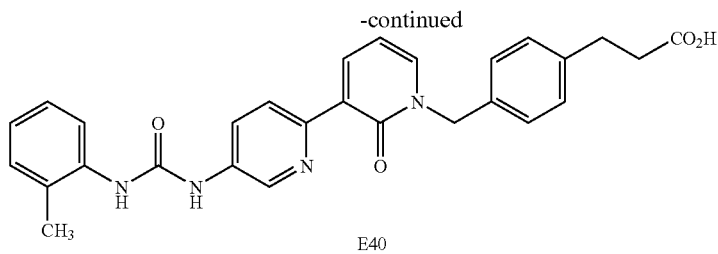

E40

EXAMPLE 41

(S)-(+)-3-{4-[2'-Oxo-5-(3-o-tolyl-ureido)-2'H-[2,3']bipyridinyl-1'-ylmethyl]-phenyl}butyric acid sodium salt (E41)

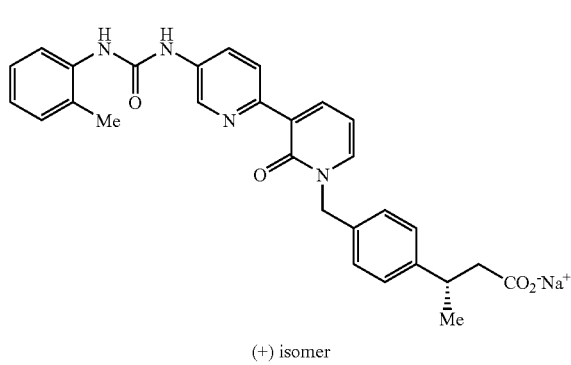

(+) isomer

The title compound was prepared as a solid from the corresponding methyl ester in a similar manner to Example 42; $[\alpha]_D^{30°\ C.}$ +12.5° (c=1.0, MeOH); MS (ES+ve): [M+H]$^+$ at m/z 497 ($C_{29}H_{28}N_4O_4$ requires [M+H]$^+$ at m/z 497).

EXAMPLE 42

(R)-(−)-3-{4-[2'-Oxo-5-(3-o-tolyl-ureido)-2'H-[2,3']bipyridinyl-1'-ylmethyl]-phenyl}butyric acid sodium salt (E42)

To a solution of the corresponding methyl ester (60 mg, 0.118 mmol) in tetrahydrofuran (5 mL) was added a solution of lithium hydroxide in water (0.5M, 5 mL, 2.5 mmol). The mixture was stirred at room temperature for 3 hours. Water (50 mL) and 2M hydrochloric acid (2 mL) were added. To the resulting suspension was added saturated sodium bicarbonate (5 mL), then the solution was passed through a 10 g tC18 Sep-Pak® cartridge (Waters). The column was washed through with dilute sodium bicarbonate, then eluted with water/methanol mixtures to give after evaporation the title compound as a solid; $[\alpha]_D^{30°\ C.}$ −12.3° (c=1.0, MeOH). MS (ES+ve): [M+H]$^+$ at m/z 497 ($C_{29}H_{28}N_4O_4$ requires [M+H]$^+$ at m/z 497).

EXAMPLE 43

(R)-(−)-3-{4-[2-Oxo-6'-(3-o-tolyl-ureido)-2H-[3,3']bipyridinyl-1-ylmethyl]-phenyl}butyric acid hydrochloric acid salt (E43)

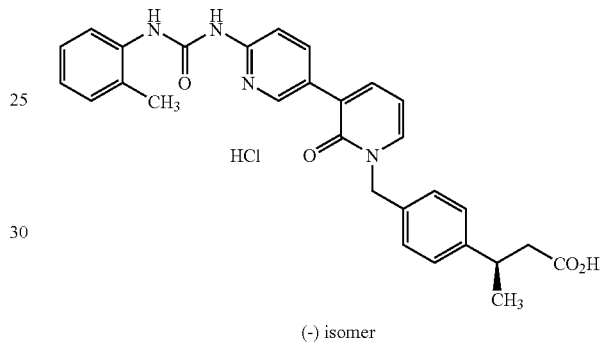

(−) isomer

The compound of Example 43 was prepared as a solid by the method of Example 11.
MS (APCI+ve): [M+H]$^+$ at m/z 497 ($C_{29}H_{28}N_4O_4$·HCl requires [M+H]$^+$ at m/z 497). $[\alpha]_D^{29.4°\ C.}$ −10.7° (c=1.0, MeOH).

EXAMPLE 44

(R)-(−)-3-{4-[2'-Oxo-5-(3-phenyl-ureido)-2'H-[2,3']bipyridinyl-1'-ylmethyl]-phenyl}butyric acid hydrochloric acid salt (E44)

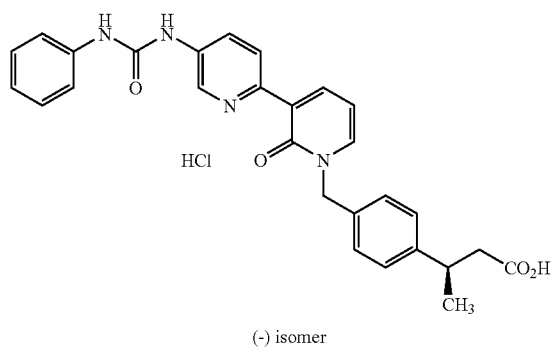

(−) isomer

The compound of Example 44 was prepared as a solid by the method of Example 11.
MS (APCI+ve): [M+H]$^+$ at m/z 483 ($C_{28}H_{26}N_4O_4$·HCl requires [M+H]$^+$ at m/z 483) $[\alpha]_D^{26°\ C.}$ −13.2° (c=0.5, MeOH)

EXAMPLE 45

(R)-(−)-3-(4-{5-[3-(2-Fluorophenyl)-ureido]-2'-oxo-2H-[2,3']bipyridinyl-1'-ylmethyl}phenyl)butyric acid hydrochloric acid salt (E45)

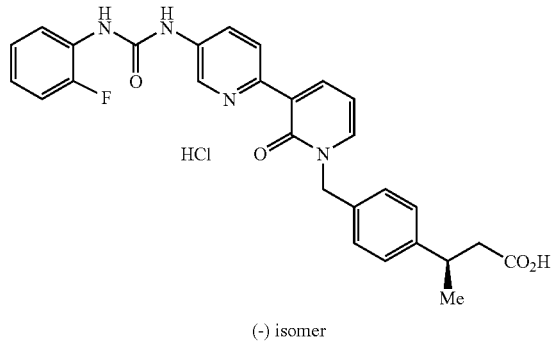

(−) isomer

The compound of Example 45 was prepared as a solid by the method of Example 11.

MS (APCI+ve): [M+H]$^+$ at m/z 501 ($C_{28}H_{25}FN_4O_4$.HCl requires [M+H]$^+$ at m/z 501). [α]$_D^{29°\ C.}$ −10.3° (c=0.5, MeOH).

EXAMPLE 46

(±)-3-(3-{2-Oxo-3-[4-(3-o-tolyl-ureido)phenyl]piperidin-1-ylmethyl}phenyl)-propionic acid (E46)

The title compound was prepared in a similar manner to Example 1 except that the hydrogenation step was carried out under modified conditions as detailed in Preparation 23.

Unless otherwise stated, the Examples listed in Table 2 were prepared in an analogous manner to that of Example 46. A variation from this procedure is described below for Example 50.

TABLE 2

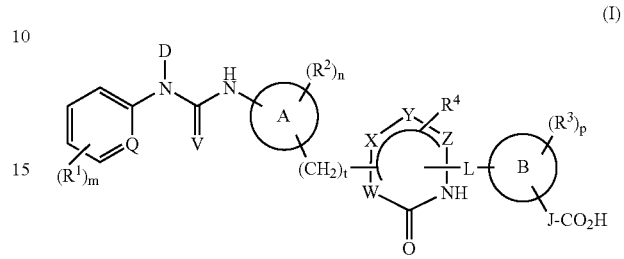

| Ex | R$^2$ | L | J | Observed* [M + H]$^+$ or [M − H]$^-$ or M$^-$ |
|---|---|---|---|---|
| E46 | H | CH$_2$ | 3-(CH$_2$)$_2$ | 484 [M − H]$^-$ |
| E47 | OMe | CH$_2$ | 4-(CH$_2$)$_2$ | 516 |
| E48 | H | CH$_2$ | 4-(CH$_2$)$_2$ | 486 |
| E49 | OMe | CH$_2$ | (±)-4-CH(Me)CH$_2$ | 530 |
| E50 | H | bond | 4-(CH$_2$)$_2$ | 472 |
| E51 | OMe | bond | 4-(CH$_2$)$_2$ | 502 |

*[M + H]$^+$ unless indicated otherwise

EXAMPLE 50

3-(4-{2-Oxo-3-[4-(3-o-tolyl-ureido)phenyl]piperidin-1-yl}phenyl)propionic acid (E50)

The title compound was prepared from 3-{4-[3-(4-nitrophenyl)-2-oxo-2H-pyridin-1-yl]phenyl}propionic acid ethyl ester which is prepared as described in Preparation 24 with subsequent hydrogenation, urea formation, and hydrolysis steps analogous to the procedures of Preparation 23, Preparation 9 and Example 1 respectively.

The invention claimed is:

1. A compound of formula (I), a carboxylic acid ester or a pharmaceutically acceptable salt thereof:

(I)

wherein
A and B are independently aryl or heteroaryl;
Q is C, CH or together with the group V or group D forms a 5-7 membered heterocyclic ring;
D is hydrogen, C$_{1-6}$alkyl or together with the group Q forms a 5-7 membered heterocyclic ring;
R$^1$, R$^2$ and R$^3$ are independently C$_{1-6}$alkyl, halogen, C$_{1-6}$alkoxy, hydroxy, cyano, CF$_3$, nitro, C$_{1-6}$alkylthio, amino, mono- or di-C$_{1-6}$alkylamino, carboxy, C$_{1-6}$alkanoyl, amido, mono- or di-C$_{1-6}$alkylamido, NHCOR$^9$ or NHSO$_2$R$^9$ in which R$^9$ is C$_{1-6}$alkyl, C$_{3-7}$cycloalkyl or phenyl (optionally substituted by up to three groups selected from C$_{1-6}$alkyl, halogen, C$_{1-6}$alkoxy, cyano, phenyl or CF$_3$) or is a group -E-(CH$_2$)$_{1-6}$NR$^x$R$^y$ in which E is a single bond or —OCH$_2$— and R$^x$ and R$^y$ are independently hydrogen, C$_{1-6}$alkyl or combine together to form a 5-7 membered heterocyclic ring;
R$^4$ is hydrogen, C$_{1-6}$alkyl, halogen or C$_{1-6}$alkoxy;
V is O, S, NH, N—C$_{1-6}$alkyl, NNO$_2$, NCN or together with the group Q forms a 5-7 membered heterocyclic ring;
W, X, Y and Z are independently C, CH or CH$_2$;
------ represents a single or double bond;
L is —(CH$_2$)$_q$— or —(CH$_2$)$_{q'}$O— where q is 0, 1, 2 or 3 and q' is 2 or 3;
J is
 (i) a group —CR$^5$=CR$^6$— where R$^5$ and R$^6$ are independently hydrogen or C$_{1-6}$alkyl; or
 (ii) a group —CHR$^7$—CHR$^8$— where R$^7$ and R$^8$ are independently hydrogen, C$_{1-6}$alkyl, C$_{3-7}$cycloalkyl, aryl, heteroaryl, a group —NHCOR$^9$— or —NHSO$_2$R$^9$— in which R$^9$ is as defined above or a group —(CH$_2$)$_{1-6}$NR$^x$R$^y$— in which R$^x$ and R$^y$ are as defined above; or
 (iii) a single bond; or
 (iv) —CHR$^6$— where R$^6$ is as defined above; or
 (v) a group —O—CHR$^{10}$—, —NR$^{11}$—CH$_7$R$^{10}$— or —CR$^{12}$R$^{13}$—CHR$^{10}$— where R$^{10}$ and R$^{11}$ are independently hydrogen or C$_{1-6}$alkyl and R$^{12}$ and R$^{13}$ are independently C$_{1-6}$alkyl or R$^{12}$ and R$^{13}$ combine together to form a C$_{3-7}$ cycloalkyl or a 5-7 membered heterocyclic ring;
m, n and p are independently 0, 1, 2 or 3; and
t is 0, 1 or 2.

2. A compound according to claim 1, wherein A is phenyl or pyridyl.

3. A compound according to claim 1 or 2, wherein B is phenyl.

4. A compound according to claim 1, wherein $R^1$, $R^2$ and $R^3$ are independently $C_{1-6}$alkyl, halogen, $C_{1-6}$alkoxy, hydroxy, cyano, $CF_3$, nitro, $C_{1-6}$alkylthio, amino, mono- or di-$C_{1-6}$alkylamino, carboxy, $C_{1-6}$alkanoyl, amido, mono- or di-$C_{1-6}$alkylamido, $NHCOR^9$ or $NHSO_2R^9$ in which $R^9$ is $C_{1-6}$alkyl, $C_{3-7}$cycloalkyl or phenyl (optionally substituted by up to three groups selected from $C_{1-6}$alkyl, halogen, $C_{1-6}$alkoxy, cyano, phenyl or $CF_3$) or is a group -E-$(CH_2)_{1-6}NR^xR^y$ in which E is a single bond or —$OCH_2$— and $R^x$ and $R^y$ are independently hydrogen, $C_{1-6}$alkyl or combine together to form a ring selected from piperidinyl, piperazinyl, pyrrolidinyl or morpholinyl group in which ring is optionally substituted by $C_{1-6}$alkyl;

When Q and V combine together to form a ring selected from piperidinyl, piperazinyl, pyrrolidinyl or morpholinyl group, which is optionally substituted by $C_{1-6}$alkyl;

When Q and D combine together to form a ring selected from piperidinyl, piperazinyl, pyrrolidinyl or morpholinyl group, which is optionally substituted by $C_{1-6}$alkyl;

J is
- (i) a group —$CR^5$=$CR^6$— where $R^5$ and $R^6$ are independently hydrogen or $C_{1-6}$alkyl; or
- (ii) a group —$CHR^7$—$CHR^8$— where $R^7$ and $R^8$ are independently hydrogen, $C_{1-6}$alkyl, $C_{3-7}$cycloalkyl, phenyl, naphthyl, thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl, pyridyl, quinolinyl, isoquinolinyl, indolyl, benzofuryl, benzothienyl, benzimidazolyl, benzoxazolyl, a group —$NHCOR^9$— or —$NHSO_2R^9$— in which $R^9$ is as defined above or a group —$(CH_2)_{1-6}NR^xR^y$— in which $NR^x$ and $R^y$ are as defined above; or
- (iii) a single bond; or
- (iv) —$CHR^6$— where $R^6$ is as defined above; or
- (v) a group —O—$CHR^{10}$—, —$NR^{11}$—$CHR^{10}$— or —$CR^{12}R^{13}CHR^{10}$— where $R^{10}$ and $R^{11}$ are independently hydrogen or $C_{1-6}$alkyl and $R^{12}$ and $R^{13}$ are independently $C_{1-6}$alkyl or $R^{12}$ and $R^{13}$ combine together to form $C_{3-7}$cycloalkyl, tetrahydropyranyl, piperidinyl, piperazinyl, pyrrolidinyl or morpholinyl;

the ring containing W, X, Y and Z is

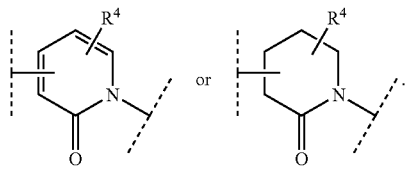

5. A compound according to claim 1, wherein $R^1$, $R^2$ and $R^3$ are independently $C_{1-6}$alkyl, halogen or $C_{1-6}$alkoxy;

Q is C, CH or together with the group V or group D form part of a benzimidazole, benzoxazole or indoline ring;

D is hydrogen, $C_{1-6}$alkyl or together with the group Q form part of a benzimidazole or benzoxazole ring;

V is O or together with the group Q form part of an indoline ring;

$R^4$ is hydrogen or halogen;

J is
- (i) a group —$CR^5$=$CR^6$— where $R^5$ and $R^6$ are independently hydrogen or $C_{1-6}$alkyl; or
- (ii) a group —$CHR^7$—$CHR^8$— where $R^7$ and $R^8$ are independently hydrogen, $C_{1-6}$alkyl, $C_{3-7}$cycloalkyl, phenyl, a group —$NHCOR^9$— in which $R^9$ is $C_{1-6}$alkyl; or
- (iii) a single bond;
- (iv) —$CHR^6$— where $R^6$ is as defined above; or
- (v) a group —O—$CHR^{10}$—, —$NR^{11}$—$CHR^{10}$— or —$CR^{12}R^{13}CHR^{10}$— where $R^{10}$ and $R^{11}$ are independently hydrogen or $C_{1-6}$alkyl and $R^{12}$ and $R^{13}$ are independently $C_{1-6}$alkyl or $R^{12}$ and $R^{13}$ combine together to form $C_{3-7}$cycloalkyl group.

6. A compound according of formula (Ia), a carboxylic acid ester or a pharmaceutically acceptable salt thereof:

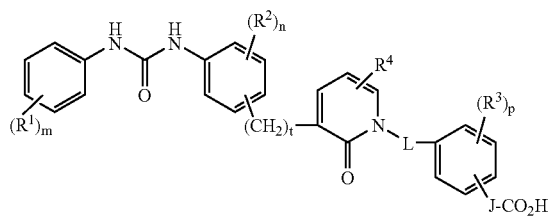

(Ia)

wherein:

$R^1$, $R^2$ and $R^3$ are independently $C_{1-6}$alkyl, halogen, $C_{1-6}$alkoxy, hydroxy, cyano, $CF_3$, nitro, $C_{1-6}$alkylthio, amino, mono- or di-$C_{1-6}$alkylamino, carboxy, $C_{1-6}$alkanoyl, amido, mono- or di-$C_{1-6}$alkylamido, $NHCOR^9$ or $NHSO_2R^9$ in which $R^9$ is $C_{1-6}$alkyl, $C_{3-7}$cycloalkyl or phenyl (optionally substituted by up to three groups selected from $C_{1-6}$alkyl, halogen, $C_{1-6}$alkoxy, cyano, phenyl or $CF_3$) or is a group -E-$(CH_2)_{1-6}NR^xR^y$ in which B is a single bond or —$OCH_2$— and $R^x$ and $R^y$ are independently hydrogen, $C_{1-6}$alkyl or combine together to form a 5-7 membered heterocyclic ring;

$R^4$ is hydrogen, $C_{1-6}$alkyl, halogen or $C_{1-6}$alkoxy;

L is —$(CH_2)_q$— or —$(CH_2)_qO$— where q is 0, 1, 2 or 3 and q' is 2 or 3;

J is
- (i) a group —$CR^5$=$CR^6$— where $R^5$ and $R^6$ are independently hydrogen or $C_{1-6}$alkyl; or
- (ii) a group —$CHR^7$—$CHR^8$— where $R^7$ and $R^8$ are independently hydrogen, $C_{1-6}$alkyl, $C_{3-7}$cycloalkyl, aryl, heteroaryl, a group —$NHCOR^9$— or —$NHSO_2R^9$— in which $R^9$ is as defined above or a group —$(CH_2)_{1-6}NR^xR^y$— in which $R^x$ and $R^y$ are as defined above; or
- (iii) a single bond; or
- (iv) —$CHR^6$— where $R^6$ is as defined above; or
- (v) a group —O—$CHR^{10}$—, —$NR^{11}$—$CH_7R^{10}$— or —$CR^{12}R^{13}$—$CHR^{10}$— where $R^{10}$ and $R^{11}$ are independently hydrogen or $C_{1-6}$alkyl and $R^{12}$ and $R^{13}$ are independently $C_{1-6}$alkyl or $R^{12}$ and $R^{13}$ combine together to form a $C_{3-7}$ cycloalkyl or a 5-7 membered heterocyclic ring;

m, n and p are independently 0, 1, 2 or 3; and t is 0, 1 or 2.

7. A compound according to claim 1 wherein:

$R^1$, $R^2$ and $R^3$ are independently $C_{1-6}$alkyl, halogen, $C_{1-6}$alkoxy, hydroxy, cyano, $CF_3$, nitro, $C_{1-6}$alkylthio, amino, mono- or di-$C_{1-6}$alkylamino, carboxy, $C_{1-6}$alkanoyl, amido, mono- or di-$C_{1-6}$alkylamido, $NHCOR^9$ or $NHSO_2R^9$ in which $R^9$ is $C_{1-6}$alkyl, $C_{3-7}$cycloalkyl or phenyl optionally substituted by up to three groups selected from $C_{1-6}$alkyl, halogen, $C_{1-6}$alkoxy, cyano, phenyl or $CF_3$;

L is —$(CH_2)_q$— where q is 0, 1, 2 or 3; and

J is
(i) a group —$CR^5$=$CR^6$— where $R^5$ and $R^6$ are independently hydrogen or $C_{1-6}$alkyl; or
(ii) a group —$CHR^7$—$CHR^8$— where $R^7$ and $R^8$ are independently hydrogen, $C_{1-6}$alkyl or a group —NH-$COR^9$— or —$NHSO_2R^9$—.

8. A compound according to claim 1, wherein J is a group —CH═CH—, —$(CH_2)_2$—, —$CHR^7$—$CH_2$— in which $R^7$ is $C_{1-6}$alkyl.

9. A compound according to claim 1 which is selected from the group consisting of 3-(4-{2-Oxo-3-[4-(3-o-tolyl-ureido)phenyl]-2H-pyridin-1-ylmethyl}phenyl)propionic acid;
3-(3-{2-Oxo-3-[4-(3-o-tolyl-ureido)phenyl]-2H-pyridin-1-ylmethyl}phenyl)propionic acid;
(4-{2-Oxo-3-[4-(3-o-tolyl-ureido)-phenyl]-2H-pyridin-1-ylmethyl}-phenoxy)-acetic acid;
4-(2-{2-Oxo-3-[4-(3-o-tolyl-ureido)-phenyl]-2H-pyridin-1-yl}-ethyl)-benzoic acid;
3-(4-{3-[3-Methoxy-4-(3-o-tolyl-ureido)-phenyl]-2-oxo-2H-pyridin-1-ylmethyl}-phenyl)-propionic acid;
(3-{2-Oxo-3-[4-(3-o-tolyl-ureido)phenyl]-2H-pyridin-1-ylmethyl}-phenoxy)-acetic acid;
3-(4-{5-Chloro-2-oxo-3-[4-(3-o-tolyl-ureido)phenyl]-2H-pyridin-1-ylmethyl}phenyl)propionic acid;
4-{2-Oxo-3-[4-(3-o-tolyl-ureido)phenyl]-2H-pyridin-1-ylmethyl}-benzoic acid;
(±)-3-(4-{2-Oxo-3-[4-(3-o-tolyl-ureido)-phenyl]-2H-pyridin-1-ylmethyl}-phenyl)-butyric acid;
(±)-3-(3-{2-Oxo-3-[4-(3-o-tolyl-ureido)-phenyl]-2H-pyridin-1-ylmethyl}-phenyl)-butyric acid;
[Methyl-(4-{2-oxo-3-[4-(3-o-tolyl-ureido)-phenyl]-2H-pyridin-1-ylmethyl}-phenyl)-amino]-acetic acid
(±)-3(4-{3-[3-Methoxy-4-(3-o-tolyl-ureido)-phenyl]-2-oxo-2H-pyridin-1-ylmethyl}-phenyl)-butyric acid;
3-(4-{2-Oxo-3-[4-(3-o-tolyl-ureido)-phenyl]-2H-pyridin-1-ylmethyl}-phenyl)-propionic acid methyl ester;
[Methyl-(3-{2-oxo-3-[4-(3-o-tolyl-ureido)-phenyl]-2H-pyridin-1-ylmethyl}-phenyl)-amino]-acetic acid;
3-(4-{2-Oxo-3-[4-(3-o-tolyl-ureido)-phenyl]-2H-pyridin-1-ylmethyl}-phenyl)-propionic acid ethyl ester;
4-(2-{2-Oxo-3-[4-(3-o-tolyl-ureido)-phenyl]-2H-pyridin-1-yl}-ethoxy)-benzoic acid;
3-(4-{2-Oxo-3-4-3-o-tolyl-ureido)-phenyl]-2H-pyridin-1-ylmethyl}-phenyl)-propionic acid cychexloxycarbonyloxymethyl ester;
3-(4-{2-Oxo-3-[4-(3-o-tolyl-ureido)-phenyl]-2H-pyridin-1-ylmethyl}-phenyl)-propionic acid isopropoxycarbonyloxymethyl ester;
3-(4-{2-Oxo-3-[4-(3-o-tolyl-ureido)-phenyl]-2H-pyridin-1-ylmethyl}-phenyl)-propionic acid acetoxymethyl ester;
3-(4-{2-Oxo-3-[4-(3-o-tolyl-ureido)-phenyl]-2H-pyridin-1-ylmethyl}-phenyl)-propionic acid isopropyl ester;
[3-(2-{2-Oxo-3-[4-(3-o-tolyl-ureido)-phenyl]-2H-pyridin-1-yl}-ethyl)-phenyl]-acetic acid;
[4-(2-{2-Oxo-3-[4-(3-o-tolyl-ureido)-phenyl]-2H-pyridin-1-yl}-ethyl)-phenyl]-acetic acid;
(±)-2-Acetylamino-3-(4-{2-oxo-3-[4-(3-o-tolyl-ureido) phenyl]-2H-pyridin-1-ylmethyl}phenyl)propionic acid;
(3-{2-Oxo-3-[4-(3-o-tolyl-ureido)-phenyl]-2H-pyridin-1-ylmethyl}-phenyl)-acetic acid;
3-[4-(3-{4-[3-(2-Fluoro-phenyl)-ureido]-3-methoxy-phenyl}-(3-oxo-2H-pyridin-1-ylmethyl)-phenyl]-propionic acid;
3-(4-{2-Oxo-3-[4-(3-phenyl-ureido)-phenyl]-2H-pyridin-1-ylmethyl}-phenyl]-propionic acid;
3-[4-(3-{4-[3-(2-Fluoro-phenyl)-ureido]-phenyl}-2-oxo-2H-pyridin-1-ylmethyl)-phenyl]-propionic acid;
3-[4-(3-{4-[3-(2,3-Difluoro-phenyl)-ureido]-phenyl}-2-oxo-2H-pyridin-1-ylmethyl-phenyl]-propionic acid;
3-[4-(3-{4-[3-(3-Fluoro-2-methyl-phenyl)-ureido]-phenyl}-2-oxo-2H-pyridin-1-ylmethyl)-phenyl]-propionic acid;
3-(4-{3-[2-Fluoro-4-(3-o-tolyl-ureido)phenyl]-2-oxo-2H-pyridin -1-ylmethyl}phenyl)propionic acid;
(S)-(+)-3-(4-{2-Oxo-3-[4-(3-o-tolylureido)phenyl]-2H-pyridin-1-ylmethyl}phenyl)butyric acid;
(R)-(−)-3-(4-{2-Oxo-3-[4-(3-o-tolylureido)phenyl]-2H-pyridin-1-ylmethyl}phenyl)butyric acid;
(±)-3-(4-{2-Oxo-3-[4-(3-o-tolyl-ureido)phenyl]-2H-pyridin-1-ylmethyl}phenyl-3-propionic acid;
(S)-(+)-3-(4-{2-Oxo-3-[4-(3-o-tolyl-ureido)phenyl]-2H-pyridin-1-ylmethyl}-phenyl)-pentanoic acid;
(R)-(−)-3-(4-{2-Oxo-3-[4-(3-o-tolyl-ureido)phenyl]-2H-pyridin-1-ylmethyl}-phenyl)-pentanoic acid;
3-Methyl-3-(4-{2-oxo-3-[4-(3-o-tolyl-ureido)-phenyl]-2H-pyridin-1-ylmethyl}-phenyl)-butyric acid;
[1-(4-{2-Oxo-3-[4-(3-o-tolyl-ureido)-phenyl]-2H-pyridin-1-ylmethyl}-phenyl)-cyclopentyl]-acetic acid;
3-(4-{2-Oxo-1-[4-(3-o-tolyl-ureido)benzyl]-1,2-dihydropyridin-3-yl}phenyl)propionic acid;
3-[4-(3-{4-[(1-2,3-Dihydroindol-1-yl-methanoyl)amino] phenyl}-2-oxo-2H-pyridin-1-ylmethyl)phenyl]propionic acid;
3-{4-[2-Oxo-5-(3-o-tolyl-ureido)-2'H-[2,3']bipyridinyl-1'-ylmethyl]phenyl}propionic acid;
(S)-(+)-3-{4-[2'-Oxo-5-(3-o-tolyl-ureido)-2'H-[2,3']bipyridinyl-1'-ylmethyl]phenyl}butyric acid sodium salt;
(R)-(−)-3-{4-[2'-Oxo-5-(3-o-tolyl-ureido)-2'H-[2,3']bipyridinyl-1'-ylmethyl]phenyl}butyric acid sodium salt;
(R)-(−)-3-{4-[2-Oxo-6'-(3-o-tolyl-ureido)-2'H-[3,3']bipyridinyl-1'-ylmethyl]phenyl}butyric acid hydrochloric acid salt;
(R)-(−)-3-{4-[2'-Oxo-5-(3-phenyl-ureido)-2'H-[2,3']bipyridinyl-1'-ylmethyl]phenyl}butyric hydrochloric acid salt;
(R)-(−)-3-(4-{5-[3-(2-Fluorophenyl)-ureido]-2'-oxo-2H-[2,3']bipyridinyl-1 '-ylmethyl}phenyl)butyric acid hydrochloric acid salt;
(±)-3-(3-{2-Oxo-3-[4-(3-o-tolyl-ureido)phenyl]piperidin-1-ylmethyl}phenyl)propionic acid;
(±)-3-(4-{3-[3-Methoxy-4-(3-o-tolyl-ureido)-phenyl]-2-oxo-piperidin-1-ylmethyl}-phenyl)-propionic acid;
(±)-3-(4-{2-Oxo-3-[4-(3-o-tolyl-ureido)-phenyl]-piperidin-1-ylmethyl}-phenyl)-propionic acid;
(±)-3-(4-{3-[3-Methoxy-4-(3-o-tolyl-ureido)-phenyl]-2-oxo-piperidin-1-ylmethyl}-phenyl)-butyric acid;
3-(4-{2-oxo-3-[4-(3-o-tolyl-ureido)phenyl]piperidin-1-yl}phenyl)propionic acid; and
(±)-3-(4-{3-[3-Methoxy-4-(3-o-tolyl-ureido)-phenyl]-2-oxo-piperidin-1-yl}-phenyl)-propionic acid;
a carboxylic acid ester or a pharmaceutically acceptable salt thereof.

10. A compound according to claim 1 which is selected from the group consisting of
3-(4-{3-[3-Methoxy-4-(3-o-tolyl-ureido)-phenyl]-2-oxo-2H-pyridin-1-ylmethyl}-phenyl)-propionic acid;

(±)-3-(4-{2-Oxo-3-[4-(3-o-tolyl-ureido)-phenyl]-2H-pyridin-1-ylmethyl}-phenyl)-butyric acid;

(R)-(−)-3-(4-{2-Oxo-3-[4-(3-o-tolylureido)phenyl]-2H-pyridin-1-ylmethyl}phenyl)butyric acid;

(S)-(−)-3-{4-[2'-Oxo-5-(3-o-tolyl-ureido)-2'H-[2,3']bipyridinyl-1'-ylmethyl]phenyl}butyric acid sodium salt; and (±)-3-(4-{3-[3-Methoxy-4-(3-o-tolyl-ureido)-phenyl]-2-oxo-piperidin-1-yl}-phenyl]-propionic acid;

a carboxylic acid ester or a pharmaceutically acceptable salt thereof.

11. A process for the preparation of a compound of formula (I) which comprises hydrolysis of a carboxylic acid ester derivative of formula (II):

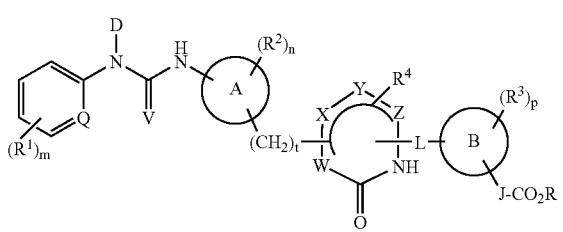

(II)

wherein

A and B are independently aryl or heteroaryl;

Q is C, CH or together with the group V or group D forms a 5-7 membered heterocyclic ring;

D is hydrogen, $C_{1-6}$alkyl or together with the group Q forms a 5-7 membered heterocyclic ring;

$R^1$, $R^2$ and $R^3$ are independently $C_{1-6}$alkyl, halogen, $C_{1-6}$alkoxy, hydroxy, cyano, $CF_3$, nitro, $C_{1-6}$alkylthio, amino, mono- or di-$C_{1-6}$alkylamino, carboxy, $C_{1-6}$alkanoyl, amido, mono- or di-$C_{1-6}$alkylamido, $NHCOR^9$ or $NHSO_2R^9$ in which $R^9$ is $C_{1-6}$alkyl, $C_{3-7}$cycloalkyl or phenyl (optionally substituted by up to three groups selected from $C_{1-6}$alkyl, halogen, $C_{1-6}$alkoxy, cyano, phenyl or $CF_3$) or is a group -E-$(CH_2)_{1-6}NR^xR^y$ in which B is a single bond or —$OCH_2$— and $R^x$ and $R^y$ are independently hydrogen, $C_{1-6}$alkyl or combine together to form a 5-7 membered heterocyclic ring;

$R^4$ is hydrogen, $C_{1-6}$alkyl, halogen or $C_{1-6}$alkoxy;

V is O, S, NH, N—$C_{1-6}$alkyl, $NNO_2$, NCN or together with the group Q forms a 5-7 membered heterocyclic ring;

W, X, Y and Z are independently C, CH or $CH_2$;

⸺ represents a single or double bond;

L is —$(CH_2)_q$— or —$(CH_2)_qO$— where q is 0, 1, 2 or 3 and q' is 2 or 3;

J is
(i) a group —$CR^5$=$CR^6$— where $R^5$ and $R^6$ are independently hydrogen or $C_{1-6}$alkyl; or
(ii) a group —$CHR^7$—$CHR^8$— where $R^7$ and $R^8$ are independently hydrogen, $C_{1-6}$alkyl, $C_{3-7}$cycloalkyl, aryl, heteroaryl, a group —$NHCOR^9$— or —$NHSO_2R^9$— in which $R^9$ is as defined above or a group —$(CH_2)_{1-6}NR^xR^y$— in which $R^x$ and $R^y$ are as defined above; or
(iii) a single bond; or
(iv) —$CHR^6$— where $R^6$ is as defined above; or
(v) a group —O—$CHR^{10}$—, —$NR^{11}$—$CH_7R^{10}$— or —$CR^{12}R^{13}$—$CHR^{10}$— where $R^{10}$ and $R^{11}$ are independently hydrogen or $C_{1-6}$alkyl and $R^{12}$ and $R^{13}$ are independently $C_{1-6}$alkyl or $R^{12}$ and $R^{13}$ combine together to form a $C_{3-7}$ cycloalkyl or a 5-7 membered heterocyclic ring;

m, n and p are independently 0, 1, 2 or 3; and t is 0, 1 or 2; and R is a group capable of forming a carboxylic acid ester and optionally thereafter forming a carboxylic acid ester or a pharmaceutically acceptable salt thereof.

12. A pharmaceutical composition which comprises a therapeutically effective amount of a compound according to claim 1, a carboxylic acid ester or a pharmaceutically acceptable salt thereof in admixture with a pharmaceutically acceptable carrier or diluent.

13. A pharmaceutical composition comprising a compound according to claim 1, a carboxylic acid ester or a pharmaceutically acceptable salt thereof together with another therapeutically active agent.

* * * * *